United States Patent
Kubota et al.

(10) Patent No.: US 11,998,115 B2
(45) Date of Patent: Jun. 4, 2024

(54) MOTORIZED FURNITURE

(71) Applicant: Paramount Bed Co., Ltd., Tokyo (JP)

(72) Inventors: Shinnosuke Kubota, Tokyo (JP); Toshihide Shiino, Tokyo (JP); Tadahiko Sakamaki, Tokyo (JP); Shunsuke Yokoo, Tokyo (JP)

(73) Assignee: Paramount Bed Co., Ltd., Tokyo (JP)

( * ) Notice: Subject to any disclaimer, the term of this patent is extended or adjusted under 35 U.S.C. 154(b) by 0 days.

(21) Appl. No.: 18/148,246

(22) Filed: Dec. 29, 2022

(65) Prior Publication Data
US 2023/0137120 A1 May 4, 2023

Related U.S. Application Data

(63) Continuation of application No. 16/639,834, filed as application No. PCT/JP2018/044703 on Dec. 5, 2018, now Pat. No. 11,571,072.

(30) Foreign Application Priority Data

Mar. 12, 2018 (JP) ................ 2018-044695
Dec. 4, 2018 (JP) ................ 2018-227422

(51) Int. Cl.
*A47C 20/04* (2006.01)
*A61M 21/02* (2006.01)
*A61M 21/00* (2006.01)

(52) U.S. Cl.
CPC .......... *A47C 20/041* (2013.01); *A61M 21/02* (2013.01); *A61M 2021/0022* (2013.01);
(Continued)

(58) Field of Classification Search
CPC ........................................ A61B 5/4806–4818
See application file for complete search history.

(56) References Cited

U.S. PATENT DOCUMENTS

2004/0103475 A1 6/2004 Ogawa et al.
2006/0106275 A1 5/2006 Raniere
(Continued)

FOREIGN PATENT DOCUMENTS

JP S63-222711 A 9/1988
JP H03-247343 A 11/1991
(Continued)

OTHER PUBLICATIONS

International Search Report PCT/ISA/210 for International Application No. PCT/JP2018/044703 dated Mar. 12, 2019.
(Continued)

*Primary Examiner* — Thaddeus B Cox
(74) *Attorney, Agent, or Firm* — Harness, Dickey & Pierce, P.L.C.

(57) ABSTRACT

A motorized furniture according to embodiments of the present invention includes a control unit. The control unit transitions to a first falling asleep operation at second time where the elapse of time since first time, where the sleep of a user of the motorized furniture is detected, is equal to or larger than a first time threshold. The control unit performs a second falling asleep operation when a variation of a signal corresponding to a biological signal of the user in a first period during the first falling asleep operation is smaller than the variation in a first prior period, which exists prior to the first period, during the first falling asleep operation or when the absolute value of a difference between the variation in the first period and the variation in the first prior period is smaller than a first variation threshold. In the second falling asleep operation, the control unit performs at least one of: an operation of decreasing the inclination of a section of the motorized furniture; an operation of decreasing the gap between the height of a head part of a mattress of the motorized furniture and the height of a waist part of the
(Continued)

mattress; and an operation of decreasing the difference between the pressure in the head part and the pressure in the waist part. The embodiments provide a motorized furniture capable of offering more comfortable sleep.

10 Claims, 16 Drawing Sheets

(52) U.S. Cl.
CPC ............ *A61M 2021/0083* (2013.01); *A61M 2205/3303* (2013.01); *A61M 2230/06* (2013.01); *A61M 2230/42* (2013.01)

(56) References Cited

U.S. PATENT DOCUMENTS

| | | | |
|---|---|---|---|
| 2007/0118054 A1* | 5/2007 | Pinhas | ............... G16H 40/67 600/587 |
| 2014/0005502 A1* | 1/2014 | Klap | ............. A61M 16/0057 600/300 |
| 2015/0136146 A1 | 5/2015 | Hood et al. | |
| 2017/0135883 A1 | 5/2017 | Franceschetti et al. | |
| 2018/0116415 A1 | 5/2018 | Karschnik et al. | |
| 2018/0214091 A1 | 8/2018 | Baker et al. | |
| 2019/0008284 A1 | 1/2019 | Gehrke et al. | |
| 2019/0117095 A1 | 4/2019 | Nakajima et al. | |

FOREIGN PATENT DOCUMENTS

| | | | |
|---|---|---|---|
| JP | 2005-214518 A | 8/2005 |
| JP | 2005-237977 A | 9/2005 |
| JP | 2005-270627 A | 10/2005 |
| JP | 2006-198023 A | 8/2006 |
| JP | 2007-222463 A | 9/2007 |
| JP | 2008-131974 A | 6/2008 |
| JP | 2008-200486 A | 9/2008 |
| JP | 2009-077940 A | 4/2009 |
| JP | 2012-34979 A | 2/2012 |
| JP | 2015-525094 A | 9/2015 |

OTHER PUBLICATIONS

Written Opinion of the International Searching Authority PCT/ISA/237 for International Application No. PCT/JP2018/044703 dated Mar. 12, 2019.

* cited by examiner

MOTORIZED FURNITURE

CROSS-REFERENCE TO RELATED APPLICATION

This is a continuation of U.S. application Ser. No. 16/639,834, filed Feb. 18, 2020, which is the National Phase under 35 U.S.C. § 371 of PCT/JP2018/044703, filed Dec. 5, 2018, now U.S. Pat. No. 11,571,072, which claims priority to Japanese Patent Application No. 2018-044695 and Japanese Patent Application No. 2018-227422, the disclosures of each of which are here by incorporated by reference in their entirety.

TECHNICAL FIELD

Embodiments of the present invention relate to a motorized furniture.

BACKGROUND ART

For example, there is a motorized furniture (such as a motorized bed or motorized chair) capable of changing its height and backrest inclination. For example, there is proposed technique of helping a user fall asleep by performing a back dropping motion when it is judged that the user falls into a sleeping state. Meanwhile, there is proposed technique of establishing an airway by dropping a headrest when snoring or apnea occurs. There is a demand for providing the user with more comfortable sleep.

CITATION LIST

Patent Literature

PTL 1: Japanese Patent Application Publication No. 2012-34979
PTL 2: Japanese Patent Application Publication No. 2005-270627

SUMMARY OF INVENTION

Technical Problem

The embodiments of the present invention provide a motorized furniture capable of offering more comfortable sleep.

Solution to Problem

A motorized furniture according to embodiments of the present invention includes a control unit. The control unit transitions to a first falling asleep operation at second time where the elapse of time since first time, where the sleep of a user of the motorized furniture is detected, is equal to or larger than a first time threshold. The control unit performs a second falling asleep operation when a variation of a signal corresponding to a biological signal of the user in a first period during the first falling asleep operation is smaller than the variation in a first prior period, which exists prior to the first period, during the first falling asleep operation or when the absolute value of a difference between the variation in the first period and the variation in the first prior period is smaller than a first variation threshold. In the second falling asleep operation, the control unit performs at least one of: an operation of decreasing the inclination of a section of the motorized furniture; an operation of decreasing the gap between the height of a head part of a mattress of the motorized furniture and the height of a waist part of the mattress; and an operation of decreasing the difference between the pressure in the head part and the pressure in the waist part. The embodiments provide a motorized furniture capable of offering more comfortable sleep.

Advantageous Effects of Invention

The embodiments of the present invention can provide a motorized furniture capable of offering more comfortable sleep.

DESCRIPTION OF EMBODIMENTS

Hereinbelow, embodiments of the present invention are described with reference to the drawings.
The drawings are schematic or conceptual, and the relationship between the thickness and width of each part, the ratio between the sizes of parts, and the like are not necessarily the same as real ones. Even when the different drawings represent the same parts, their dimensions and the ratio between them may be represented in different ways from one drawing to another.

Throughout the specification of the present application and the drawings, the same components as ones already described in the previously mentioned drawings are given the same reference signs and their detailed description is omitted as appropriate.

First Embodiment

Figure 1:
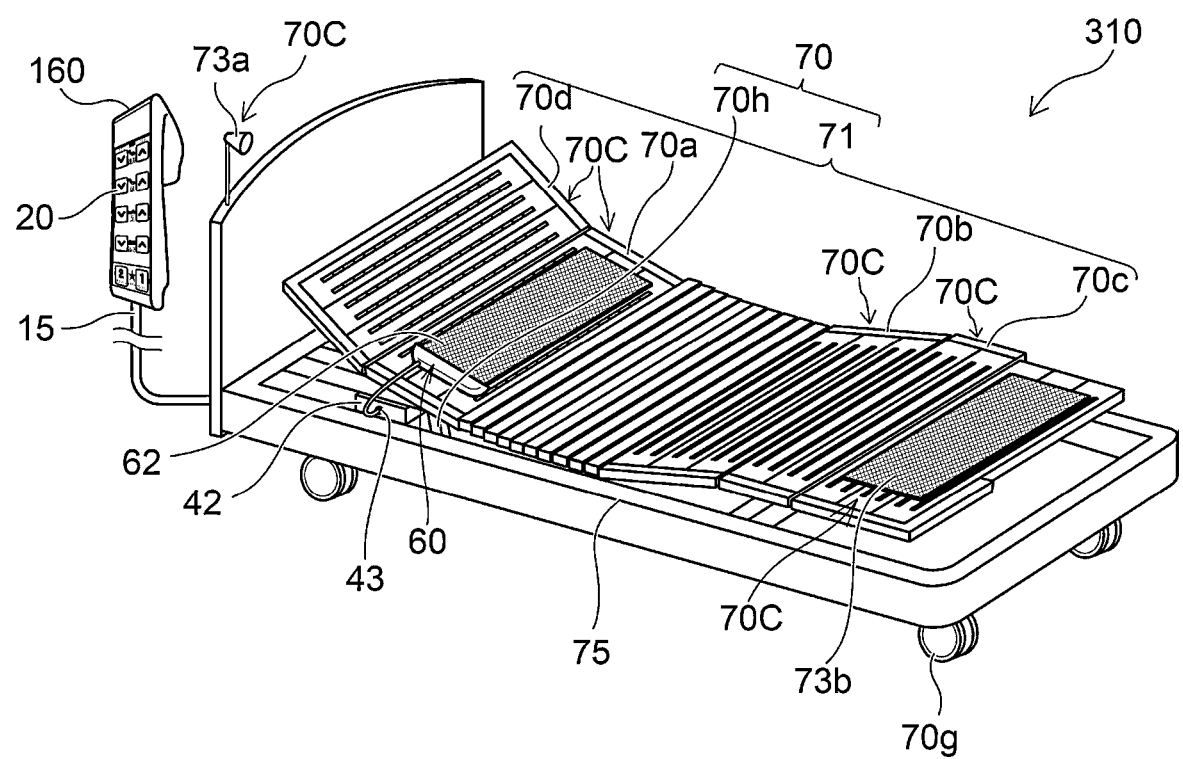
FIG. 1 is a schematic perspective view illustrating a motorized furniture according to a first embodiment of the present invention.

FIG. 1 is a schematic perspective view illustrating a motorized furniture according to a first embodiment of the present invention.

As illustrated in FIG. 1, a motorized furniture 310 according to the first embodiment includes a controlled unit 70C. The controlled unit 70C includes a movable unit 70, for example. The controlled unit 70C may include at least one of: the movable unit 70; a lighting unit 73a; and a temperature control unit 73b (such as a heater).

In this example, the motorized furniture 310 is provided with a control device 160. The control device 160 can control the controlled unit 70C of the motorized furniture 310 (such as the movable unit 70). The control device 160 is a remote controller of the motorized furniture 310, for example. The control device 160 is a handy switch, for example.

The control device 160 is provided with a manipulation reception unit 20 (such as buttons or a touch panel). The manipulation reception unit 20 is configured to receive user's manipulation. The controlled unit 70C (such as the movable unit 70) is controlled by user's operations on the manipulation reception unit 20.

The control device 160 may have various functions such as: a lighting on/off function; a nurse/carer call function; or a power on/off function.

The motorized furniture 310 is used in a location such as a house. The motorized furniture 310 may alternatively be used in a location such as an accommodation facility, a hospital, or a nursing-care facility.

In this example, the motorized furniture 310 is a motorized bed. The movable unit 70 described above is provided on the motorized bed. The movable unit 70 includes a section 71. A mattress (not illustrated in FIG. 1) is placed on the section 71. A user lies on the mattress.

The movable unit 70 includes sections such as: a back section 70a; an upper leg section 70b; a lower leg section 70c; and a height change section 70h. The height change section 70h is a bed lifting device, for example. As in the example in FIG. 1, the movable unit 70 may further include a head section 70d. The multiple sections (the back section 70a, the upper leg section 70b, the lower leg section 70c, and the head section 70d) included in the section 71 can change their angles.

For example, the angle of the user's back can be changed by the operation of the back section 70a. The angle of the knees can be changed by the operations of the upper leg section 70b and the lower leg section 70c. The angle of the head part (or the height of the head part) of the user can be changed by the operation of the head section 70d. These angles can change in conjunction with each other. These angles are angles relative to a frame 75 of the bed. The frame 75 is set substantially in parallel with the floor surface, for example. The above angles of the section 71 may be angles relative to the floor surface. In this example, casters 70g are arranged below the frame 75. The casters 70g may be replaced with "legs".

The height change section 70h can change the distance (height) between the floor surface and the bed surface. The height change section 70h may be capable of changing the height of the bed on the head side and the height of the bed on the foot side individually. This makes it possible to change the inclination of the whole bed surface.

An actuator is used for these sections of the movable unit 70, for example. The operation of the movable unit 70 enables at least one of motions including: a "back raising" motion; a "knee raising" motion; a "height adjustment" motion; an "inclination" motion; and the like. The "inclination" motion includes at least done of a roll motion and a tilt motion.

The control device 160 is electrically connected to the controlled unit 70C (the movable unit 70, for example). A control circuit may be provided between the control device 160 and the movable unit 70. The electrically connected state also includes such a case where another circuit is provided in between.

In the example of FIG. 1, the control device 160 is connected to the motorized furniture 310 via a cable 15. The control device 160 may be connected to the motorized furniture 310 via wireless communication. The control device 160 may be capable of communicating with the controlled unit 70C by any method.

The control device 160 is manipulated by the user or the like (the user or a carer of the user). This enables manual control over the controlled unit 70C (the movable unit 70, for example).

In the embodiment, automatic control is possible in addition to the manual control by the user. In the automatic control, the controlled unit 70C (the movable unit 70, for example) is controlled without operations by the user or the like, for example. This control is carried out by a control unit 42, for example. In the example illustrated in FIG. 1, the control unit 42 is provided below the section 71. The control unit 42 may be provided in the control device 160 (a remote controller or a handy switch). The control unit 42 may be provided at any location.

In the embodiment, the control unit 42 controls the controlled unit 70C (the movable unit 70, for example) based on a biological signal of the user.

The biological signal includes a signal (such as information) on the body movement of the user. The biological signal includes a signal (such as information) on at least one of the respiratory rate and heartbeat rate of the user. For example, the biological signal may include a signal (such as information) on at least one of motions of the arms, torso, and feet of the user. For example, the biological signal may include a signal (such as information) on the rolling over of the user.

The biological signal is detected by a detection unit 60, for example. As will be described later, a sensor 62 is used as the detection unit 60. In the example illustrated in FIG. 1, the sensor 62 is placed on the section 71. For example, the sensor 62 is provided between the section 71 and the mattress. For example, a detection result detected by the detection unit 60 is supplied to an acquisition unit 43 (an I/O port, for example). The detection result is supplied from the acquisition unit 43 to the control unit 42.

An example of the automatic control by the control unit 42 will be described later. First, an example of the manual control is described below.

FIGS. 2A to 2F are schematic diagrams illustrating control over the motorized furniture according to the first embodiment.

Figure 2A:
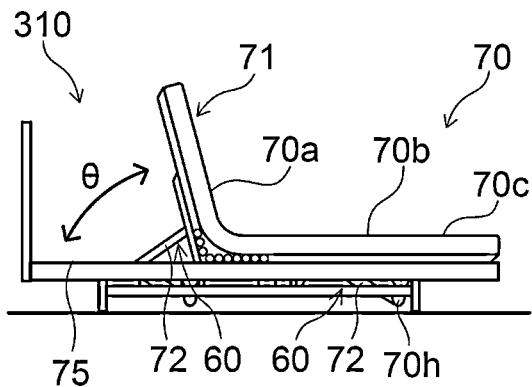
FIGS. 2A to 2F are schematic diagrams illustrating control over the motorized furniture according to the first embodiment.
Figure 2B:
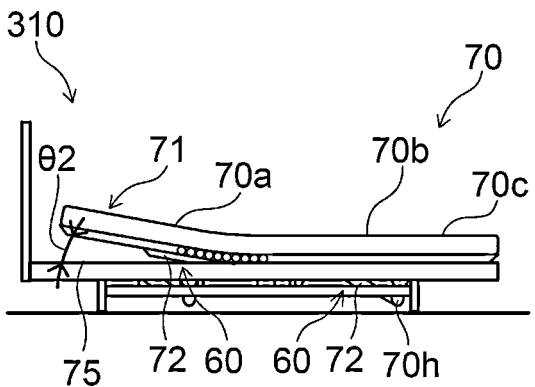
Figure 2C:
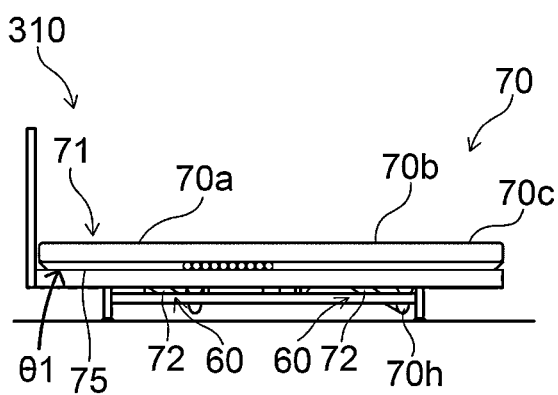

In the example of FIGS. 2A to 2F, the back section 70a, the upper leg section 70b, the lower leg section 70c, and the height change section 70h are arranged. As illustrated in FIG. 2A, the inclination (angle) of the back section 70a is changed by operations on the control device 160 (the manipulation reception unit 20, for example) by the user or the like. For example, a "back raising motion" or a "back dropping motion" is performed. The inclination of the section 71 (the back section 70a, for example) is inclination in relation to the frame 75 of the bed. The inclination of the section 71 (the back section 70a, for example) may be an angle relative to the floor surface.

For example, assume that the angle between the back section 70a and the frame 75 is a section angle θ. The section angle θ is changed by operating the control device 160. In the example illustrated in FIG. 2B, the section angle θ is a second angle θ2. The second angle θ2 is equal to or larger than 3 degrees and equal to or smaller than 10 degrees, for example. In the example illustrated in FIG. 2C, the section angle θ is a first angle θ1. The first angle θ1 is substantially 0 degree (smaller than 3 degrees, for example).

Figure 2D:
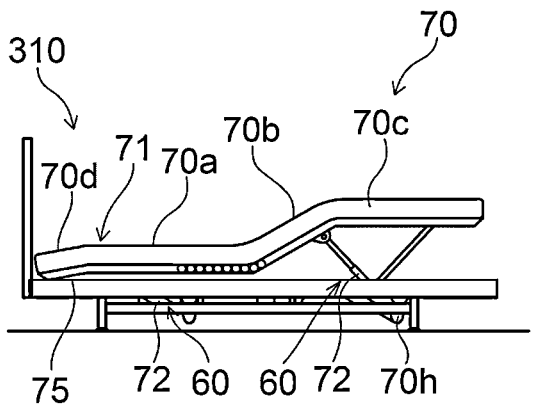

As illustrated in FIG. 2D, the angles of the upper leg section 70b and the lower leg section 70c may be changed by operations on the manipulation reception unit 20. A "knee raising motion" or a "knee dropping motion" is performed. As illustrated in FIG. 2D, the head section 70d may incline in a reverse direction so as to be located below the back section 70a.

Figure 2E:
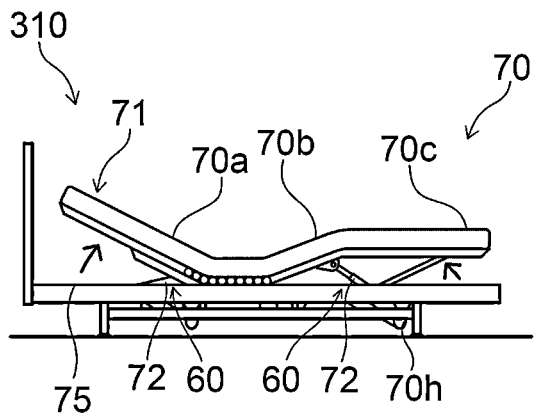

As illustrated in FIG. 2E, the angles of the back section 70a, the upper leg section 70b, and the lower leg section 70c may be changed in conjunction with each other by operations on the manipulation reception unit 20.

Figure 2F:
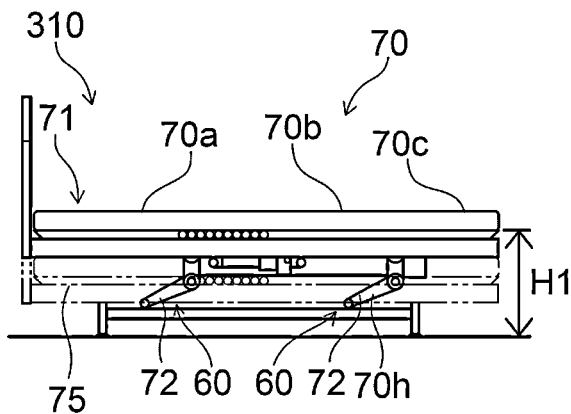

As illustrated in FIG. 2F, the motion of the height change section 70h is controlled by operations on the manipulation reception unit 20. Thereby, the height adjustment is performed. Specifically, a height H1 of the bed surface is changed. The angle of the section 71 and the height H1 may be changed at the same time.

As illustrated in FIGS. 2A to 2F, a driving unit 72 (such as an actuator) is provided in the motorized furniture 310. The movable unit 70 is moved by the operation of the driving unit 72.

In one example, the driving unit 72 may include a load sensor (such as a load cell). The biological signal of the user of the motorized furniture 310 may be detected by a load applied on the load sensor (the driving unit 72). This corresponds to a case where the driving unit 72 that drives the movable unit 70 is provided with the detection unit 60. In this way, the detection unit 60 may be included in the driving unit 72.

Hereinbelow, a description is given of a case where the detection unit 60 includes the sensor 62. The sensor 62 is provided separately from the driving unit 72.

Hereinbelow, a functional block example of the motorized furniture 310 is described.

Figure 3:
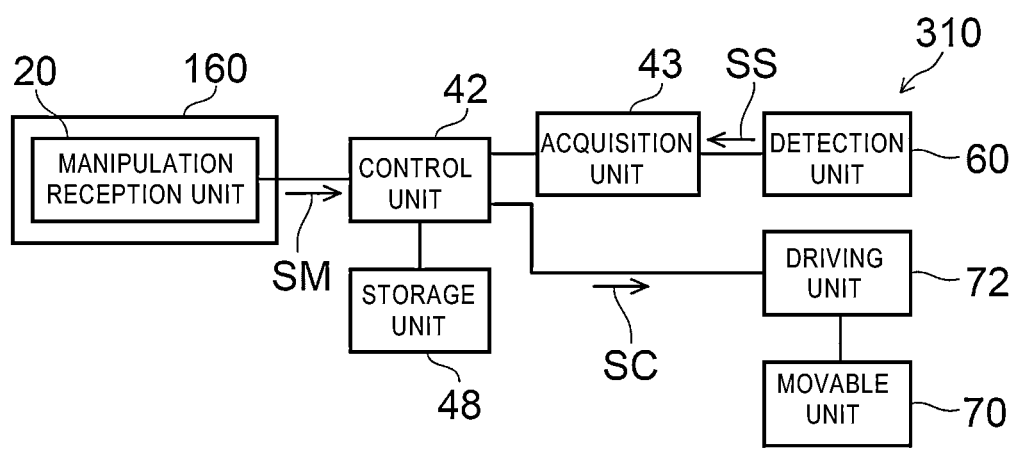
FIG. 3 is a block diagram illustrating the motorized furniture according to the first embodiment.

FIG. 3 is a block diagram illustrating the motorized furniture according to the first embodiment.

As illustrated in FIG. 3, the motorized furniture 310 is provided with the control unit 42, the acquisition unit 43, the detection unit 60, the driving unit 72, the movable unit 70 (the controlled unit 70C), and the control device 160, for example. In this example, the detection unit 60 is included in the motorized furniture 310. In the embodiment, the detection unit 60 may be provided separately from the motorized furniture 310.

The control device 160 that includes the manipulation reception unit 20 is connected to the control unit 42. The control unit 42 is connected to the driving unit 72. Based on a signal SM that is output in response to operations the manipulation reception unit 20 has received, a control signal SC is supplied from the control unit 42 to the driving unit 72. The driving unit 72 drives the movable unit 70 upon receipt of the control signal SC, whereby the movable unit 70 moves. As has been described, when the driving unit 72 (such as an actuator) includes a load sensor, at least a part of the driving unit 72 may be regarded as the detection unit 60.

In the embodiment, a storage unit 48 may be provided. The storage unit 48 may store therein various kinds of user state information and movable unit information. The user state information is information on user's state. The movable unit information is information on movable unit's state. The movable unit information is associated with the user state information. The control unit 42 may perform processing while retrieving information stored in the storage unit 48 as needed. For example, a part of the operation of the movable unit 70 may be prohibited for some users. For example, the operation range (such as the angle range) of the movable unit 70 may be restricted. The user state information includes such a prohibited matter or restricted matter. The movable unit information includes information on the movable unit 70's operation state associated with this user state information.

Meanwhile, the detection unit 60 is configured to detect the user's state. A signal SS (detection signal) corresponding to the biological signal detected and acquired by the detection unit 60 is supplied to the acquisition unit 43. The acquisition unit 43 is an I/O port, for example. The acquisition unit 43 is an interface of the signal SS, for example.

The signal SS acquired by the acquisition unit 43 is supplied to the control unit 42. The control unit 42 is a processor, for example. An electronic circuit (such as a computer) may be used as the control unit 42, for example. The control unit 42 is configured to control the movable unit 70 based on the signal SS corresponding to the biological signal.

The block diagram illustrated in FIG. 3 illustrates functional blocks. Multiple functions may be implemented by one part (such as a circuit). For example, at least a part of the function of the control unit 42 may be implemented by the detection unit 60. The acquisition unit 43 may be regarded as a part of the control unit 42.

Hereinbelow, a description is given of an example of control based on the biological signal. In the embodiment, the biological signal includes at least one of the respiratory rate and heartbeat rate of the user, for example. The respiratory rate is the number of breaths per unit time. The heartbeat rate is the number of heartbeats per unit time. The unit time is one minute, for example. These biological signals are associated with human's (user's) state.

Further, the biological signal varies with time according to the human's state. For example, during waking hours, the biological signal is likely to vary with human activities. For example, during sleep, the variation of the biological signal (such as the respiratory rate and the heartbeat rate) is smaller than that of the biological signal during waking hours. For example, during sleep, the variation of at least one of motions of the arms, torso, and feet of the user is smaller than during waking hours.

During sleep, the biological signal also varies with a sleep state. As one example, REM sleep and non-REM sleep occur during human sleep. During REM sleep, a low-amplitude brain wave similar to that during waking hours occurs. REM sleep is accompanied with rapid eye movement. During non-REM sleep, a spindle wave or a high-amplitude δ wave occurs in a brain wave. For example, a variation of the biological signal during REM sleep is larger than a variation of the biological signal during non-REM sleep.

More comfortable sleep can be assumed to be provided by establishing a state where REM sleep and non-REM sleep occur properly, for example.

In the embodiment, the motorized furniture 310 is provided with the acquisition unit 43 and the control unit 42. The acquisition unit 43 is configured to acquire the signal SS (detection signal) corresponding to the biological signal of the user of the motorized furniture 310 that includes the movable section 71. For example, the signal SS corresponding to the biological signal includes information on at least one of the respiratory rate and heartbeat rate of the user. The signal SS may include information on the motion of at least one of the arms, torso, and feet of the user. The signal SS may include information on the rolling over of the user. The signal SS may include a signal on the number of the rolling over of the user.

The control unit 42 is configured to control the controlled unit 70C (such as the movable unit 70) according to a variation of this signal SS. The control unit 42 supplies the control signal SC to the driving unit 72 based on the variation of the signal SS. Thereby, the operation of the section 71 is controlled according to the variation of the signal SS. Specifically, according to the variation of the signal SS, the control unit 42 controls the section 71 (e.g. the inclination of the section 71), for example. The angle of the section 71 is the section angle $\theta$ illustrated in FIG. 2A, for example. For example, the control unit 42 increases or decreases the inclination of the section 71 (the section angle $\theta$) according to the variation of the signal SS. As a result, the motorized furniture 310 is automatically driven according to the user's sleep state.

Hereinbelow, a description is given of an example of changing the section angle $\theta$ according to the variation of the signal SS.

Figure 4A:
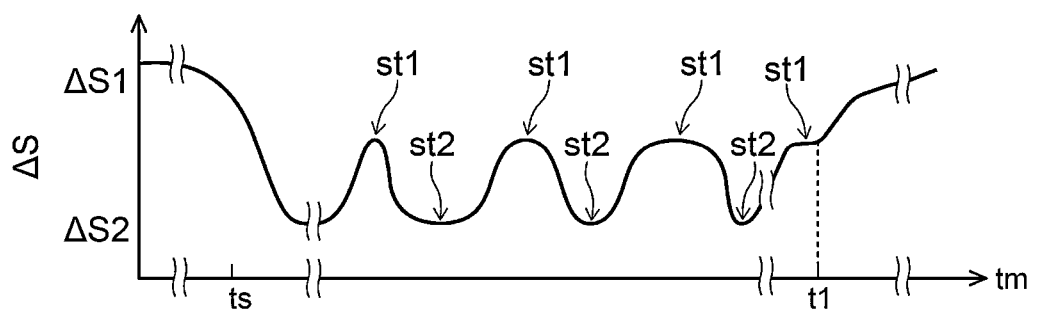
FIGS. 4A and 4B are schematic diagrams illustrating operations of the motorized furniture according to the first embodiment.
Figure 4B:
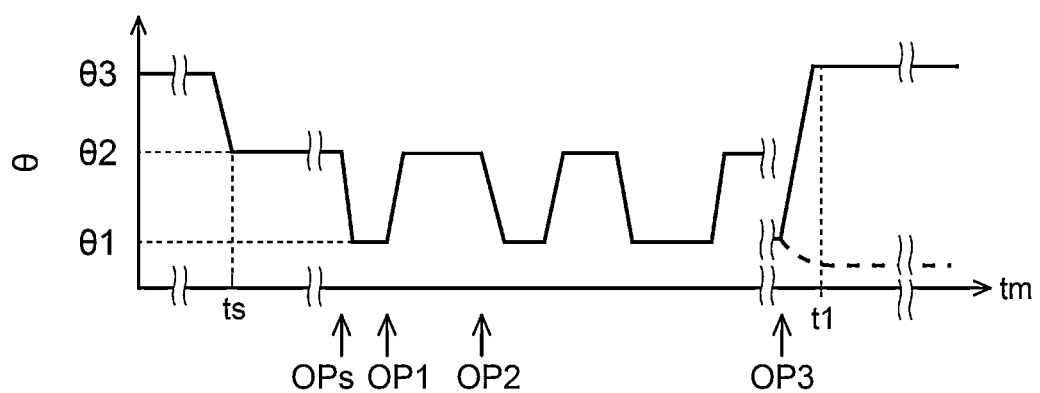

FIGS. 4A and 4B are schematic diagrams illustrating operations of the motorized furniture according to the first embodiment.

The horizontal axis of these drawings is time tm.

The longitudinal axis of FIG. 4A indicates a variation $\Delta S$ of the signal SS. In the longitudinal axis of FIG. 4A, a variation $\Delta S1$ is larger than a variation $\Delta S2$. The variation $\Delta S$ includes at least one of a temporal change in the signal SS and a change in the amplitude of the signal SS. For example, the variation $\Delta S$ observed when a period between the minimum value and the maximum value of the signal SS is short is larger than the variation $\Delta S$ observed when the period between the minimum value and the maximum value of the signal SS is long. For example, the variation $\Delta S$ observed when the difference (amplitude) between the minimum value and the maximum value of the signal SS is large is larger than the variation $\Delta S$ observed when the difference (amplitude) between the minimum value and the maximum value of the signal SS is small.

The longitudinal axis of FIG. 4B is an angle (the section angle $\theta$). For example, a back raising angle changes according to the section angle $\theta$. For example, the first angle $\theta1$ is substantially 0 degree. At this time, the upper surface of the section 71 (bed) is flat. The second angle $\theta2$ is equal to or larger than 3 degrees and equal to or smaller than 10 degrees, for example. At this time, the upper surface of the section 71 (bed) slightly inclines. For example, a third angle $\theta3$ of the section angle $\theta$ is larger than the second angle $\theta2$. The third angle $\theta3$ is larger than 10 degrees, for example.

When the section angle $\theta$ is equal to or larger than 3 degrees and smaller than 12 degrees, it has a curative effect against orthostatic hypotension, for example. Experimental result shows that, when the section angle $\theta$ is 20 degrees, sleep becomes significantly uncomfortable as compared with when the section angle $\theta$ is 10 degrees, for example.

For example, it is assumed that the user can roll over easily when the upper surface of the section 71 (bed) is flat (the first angle $\theta1$, for example). On the other hand, the user can fall asleep easily when the section 71 (the back section 70a) inclines gently (the second angle $\theta2$, for example). Further, when the user is awake, the user often finds it natural that the inclination of the section 71 (the back section 70a) is large (the third angle $\theta3$, for example).

In the embodiment, the angle of the section 71 (the section angle $\theta$, for example) is changed according to the variation $\Delta S$ of the signal SS that corresponds to the biological signal.

For example, the control unit 42 performs a first operation OP1. The first operation OP1 is an operation performed when the variation $\Delta S$ of the signal SS decreases. In the first operation OP1, the control unit 42 increases the inclination of the section 71 (the section angle $\theta$, for example) when the variation $\Delta S$ of the signal SS decreases. For example, in the first operation OP1, the control unit 42 increases the section angle $\theta$ from the first angle $\theta1$ to the second angle $\theta2$. For example, the control unit 42 increases the section angle $\theta$ when the variation $\Delta S$ of the signal SS tends to decrease after the peak (maximum) of the variation $\Delta S$ is over.

For example, the user's sleep is becoming deeper when the variation $\Delta S$ of the signal SS decreases. By increasing the section angle $\theta$ from the first angle $\theta1$ to the second angle $\theta2$ at this stage, it is possible to help the user's deeper sleep. For example, this can make the user sleep deeply earlier. Thereby, it is possible to provide more comfortable sleep.

The control unit 42 may further perform a second operation OP2. The second operation OP2 is an operation performed when the variation $\Delta S$ of the signal SS increases. In the second operation OP2, the control unit 42 decreases the inclination of the section 71 (the section angle $\theta$, for example) when the variation $\Delta S$ of the signal SS increases. For example, in the second operation OP2, the control unit 42 decreases the section angle $\theta$ from the second angle $\theta2$ to the first angle $\theta1$. For example, the control unit 42 decreases the section angle $\theta$ when the variation $\Delta S$ of the signal SS tends to increase after the section (minimum) of the variation $\Delta S$ is over.

When the variation $\Delta S$ of the signal SS increases, the user often tries to roll over. At this time, the control unit makes the upper surface of the bed flat by decreasing the section angle $\theta$ to the first angle $\theta1$. This helps the user roll over more easily and reduces the user's burden. Thereby, it is possible to provide more comfortable sleep.

Further, the control unit performs the first operation OP1 after the second operation OP2. This can help the user sleep deeply earlier after he/she rolls over, for example. The control unit iterates these first operation OP1 and second operation OP2. Thereby, it is possible to provide high-quality sleep.

In this way, in the first operation OP1, the control unit 42 changes the angle (the section angle $\theta$) from the first angle $\theta1$ to the second angle $\theta2$. The first angle $\theta1$ is an angle observed when the variation $\Delta S$ of the signal SS is in a first state. The second angle $\theta2$ is an angle observed when the variation $\Delta S$ of the signal SS is in a second state. The second state comes after the first state, and the variation $\Delta S$ in the second state is smaller than the variation $\Delta S$ in the first state.

Further, in the second operation OP2, the control unit 42 changes the angle (the section angle θ) to an angle smaller than the second angle θ2 (the first angle θ1, for example) in a third state. The third state comes after the second state, and the variation ΔS in the third state is larger than the variation ΔS in the second state.

For example, the signal SS includes multiple states (e.g. a first signal state st1 and a second signal state st2: see FIG. 4A). As illustrated in FIG. 4A, the variation ΔS of the signal SS in the second signal state st2 is smaller than the variation ΔS of the signal SS in the first signal state st1.

For example, the first signal state st1 is assumed to correspond to REM sleep. For example, the second signal state st2 is assumed to correspond to non-REM sleep.

For example, the first operation OP1 corresponds to the operation observed when the first signal state st1 transitions to the second signal state st2. The first operation OP1 corresponds to the operation observed when REM sleep transitions to non-REM sleep. The second operation OP2 corresponds to the operation observed when the second signal state st2 transitions to the first signal state st1. The second operation OP2 corresponds to the operation observed when non-REM sleep transitions to REM sleep.

The control unit 42 may further perform a third operation OP3 in addition to these first operation OP1 and second operation OP2. The third operation OP3 is an operation performed when the user gets up at predetermined time t1 (see FIG. 4A).

As described above, the signal SS includes the first signal state st1 and the second signal state st2. The control unit 42 performs the third operation OP3 when the signal SS becomes the first signal state st1 at the time before and closest to the predetermined time t1. In the third operation OP3, the control unit sets the inclination of the section 71 (the section angle θ) larger than the inclination increased as described above (the second angle θ2), for example. The third operation OP3 helps the user wake up, for example. In the third operation OP3, the section angle θ may be changed to the third angle θ3 by way of the state of the second angle θ2.

Thereby, the user can wake up comfortably. For example, when the user is in REM sleep at the time closest to the predetermined time t1, an increase of the section angle θ can wake the user up.

In the third operation OP3, the section 71 may be inclined (the section angle θ) at a reverse angle (negative angle: a broken line in FIG. 4B) according to the state (or taste) of the user (see the head section 70d in FIG. 2D). In this case, the head part of the user inclines below the torso. The angle in the third operation OP3 may be changed according to the state (such as the age, health conditions, and taste) of the user.

As illustrated in FIG. 4B, the control unit 42 may perform a falling asleep operation OPs. For example, at time ts, the user or the like makes an input indicating that the user wishes to fall asleep by manipulating the control device 160. In this example, the section angle θ is large (the third angle θ3, for example) in a state before the time ts. In the state before the time ts, the section angle θ may be set at any value and may be 0 degree, for example. When the falling asleep manipulation is made at the time ts, the control unit 42 sets the section angle θ at the second angle θ2. This helps the user fall asleep. Then, when the variation ΔS of the signal SS corresponding to the biological signal becomes smaller, for example, the control unit 42 may decrease the section angle θ to the first angle θ1. Alternatively, when the variation ΔS of the signal SS corresponding to the biological signal increases again after the decrease, the control unit 42 may increase the section angle θ to the second angle θ2. This operation corresponds to the first operation OP1.

In the embodiment, for example, the control unit 42 may change the angle (the angle according to the variation ΔS of the signal SS) in the first operation OP1 or the second operation OP2 based on the relationship between past data on the variation ΔS of the signal SS and the angle of the section 71 (the section angle θ). For example, the section angle θ that brings comfortable sleep sometimes differs from one user to another. In addition, the section angle θ that brings comfortable sleep to each user sometimes differs between an initial period and later period of sleep. In this case, for example, the control unit may change the section angle θ to be set based on the relationship between the past data on the variation ΔS of the signal SS and the angle of the section 71 (the section angle θ). In other words, the control unit may set more appropriate section angle θ by learning the relationship between the past data on the variation ΔS of the signal SS and the section angle θ. For example, by learning, the control unit may customize and change the inclination (such as the angle) of at least one of the multiple factors included in the section 71 taken in at least one of the states where the user is falling asleep and where the user is already asleep.

In the above example, the angle that is changed according to the variation ΔS of the signal SS corresponding to the biological signal is the angle of the back section 70a. In the embodiment, the angle of another portion included in the section 71 may be controlled according to the variation ΔS of the signal SS corresponding to the biological signal.

The motorized furniture 310 (see FIG. 1) according to this embodiment includes the control unit 42 capable of the above operations. The control unit 42 may include the above acquisition unit 43, or the acquisition unit 43 may be provided separately from the control unit 42. The motorized furniture 310 includes the controlled unit 70C (the movable unit 70, for example). The motorized furniture 310 may further include the above detection unit 60. An apneic state, snoring, or the like may be suppressed by the operations of the embodiment.

In the above example, the user's sleep state is presumed based on the biological signal, and the movable unit 70 is controlled according to the sleep state. In the embodiment, the user's posture (such as a supine position, a prone position, or a lateral position) may be presumed. The movable unit 70 may be controlled according to the presumption result of the user's posture.

Hereinbelow, a description is given of an example of a flowchart of the motorized furniture according to this embodiment.

Figure 5:
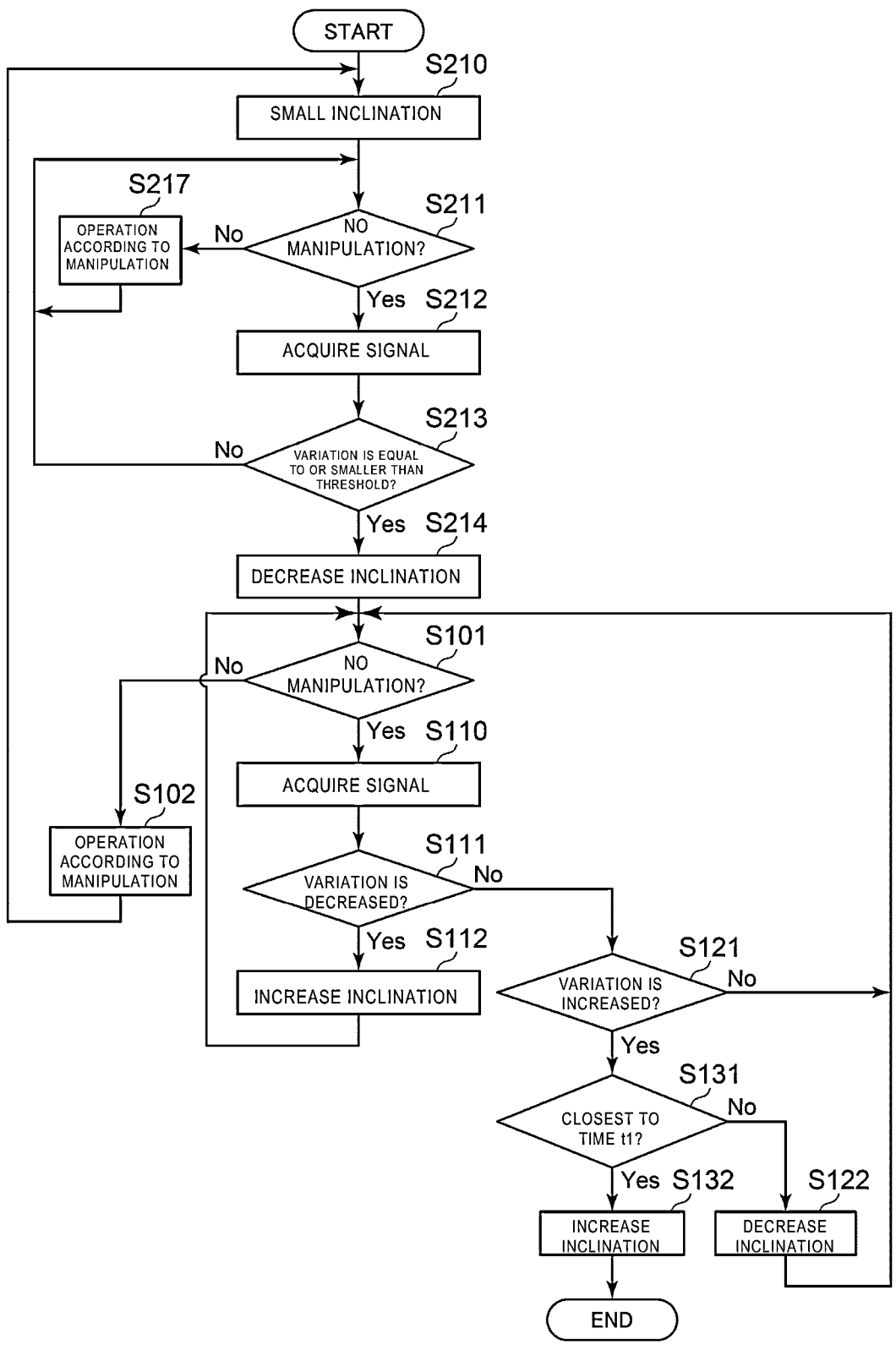
FIG. 5 is a flowchart illustrating the operations of the motorized furniture according to the first embodiment.

FIG. 5 is a flowchart illustrating the operations of the motorized furniture according to the first embodiment.

For example, an input indicating that the user wishes to fall asleep is made by manipulating the control device 160. Thereby, as illustrated in FIG. 5, the section 71 (the back section 70a, for example) takes a small inclination (the second angle θ2, for example)(Step S210).

For example, it is judged, in a predetermined period, whether or not manipulation on the control device 160 is performed (Step S211). If the manipulation is performed (if "NO"), the control unit operates the section 71 according to the manipulation (Step S217). For example, if a back raising manipulation input is made, the control unit performs back raising manual control. Then, the process returns back to Step S211.

In Step S211, if no manipulation on the control device 160 is performed (if "YES"), the control unit performs automatic control described below.

If no manipulation is performed (in the case of automatic control), the signal SS corresponding to the biological signal is acquired (Step S212). Then, it is judged whether or not the variation ΔS of the signal SS is equal to or smaller than a threshold (Step S213). If the variation ΔS of the signal SS is not equal to or smaller than the threshold, the process returns back to Step S211.

In Step S213, if it is judged that the variation ΔS of the signal SS is equal to or smaller than the threshold, the control unit decreases the inclination of the section 71 (the back section 70a, for example)(Step S214). For example, the control unit sets the section angle θ at the above first angle θ1. Steps S213 and S214 correspond to the falling asleep operation OPs, for example.

It is further judged whether or not manipulation on the control device 160 is performed (Step S101). If it is judged that manipulation is performed (if "NO"), the control unit operates the section 71 according to the manipulation (Step S102). Then, the process returns back to Step S210, for example. The process may return back to Step S211 or Step S101 after Step S102.

In Step S101, if no manipulation is performed (if "YES"), the signal SS corresponding to the biological signal is acquired (Step S110).

It is further judged whether or not the variation ΔS of the signal SS is decreased, for example (Step S111). If the variation ΔS is decreased, the control unit increases the inclination of the section 71 (the back section 70a) (Step S112). For example, the control unit sets the section angle θ at the above second angle θ2. Whether or not the variation ΔS is decreased is judged using the threshold regarding the decrease of the variation ΔS, for example. Then, the process returns back to Step S101, for example. Step S111 and Step S112 correspond to the above first operation OP1. The first operation OP1 helps the user sleep.

In Step S111, if the variation ΔS is not decreased, it is judged whether or not the variation ΔS is increased (Step S121). Whether or not the variation ΔS is increased is judged using the threshold regarding the increase of the variation ΔS, for example.

In Step S121, if the variation ΔS is not increased, it means there is substantially no change in the variation ΔS. In this case, the process returns back to Step S101.

In Step S121, if the variation ΔS is increased (i.e. if in the first signal state st1 where the variation ΔS is large), it is judged whether or not this first signal state st1 is the first signal state st1 at the time before and closest to the predetermined time t1 (Step S131).

In Step S131, if this first signal state is not at the time closest to the time t1 (if "NO"), the control unit decreases the inclination of the section 71 (Step S122). For example, the control unit sets the section angle θ at the first angle θ1. Then, the process returns back to Step S101, for example. Step S121 and Step S122 correspond to the above second operation OP2. The second operation OP2 helps the user roll over more easily, for example.

In Step S131, if it is judged that this first signal state st1 is the first signal state st1 at the time before and closest to the time t1, the control unit increases the inclination of the section 71 (e.g. the control unit sets the section angle θ at the third angle θ3)(Step S132). This helps the user wake up comfortably.

In the above process, some Steps may be swapped each other within a technically possible range. For example, Step S111 and Step S121 may be swapped each other. In this case, Step S112 and Step S122 are also swapped in conjunction with this.

Second Embodiment

In this embodiment, the shape of the mattress is changed based on the signal SS corresponding to the biological signal.

Figure 6:
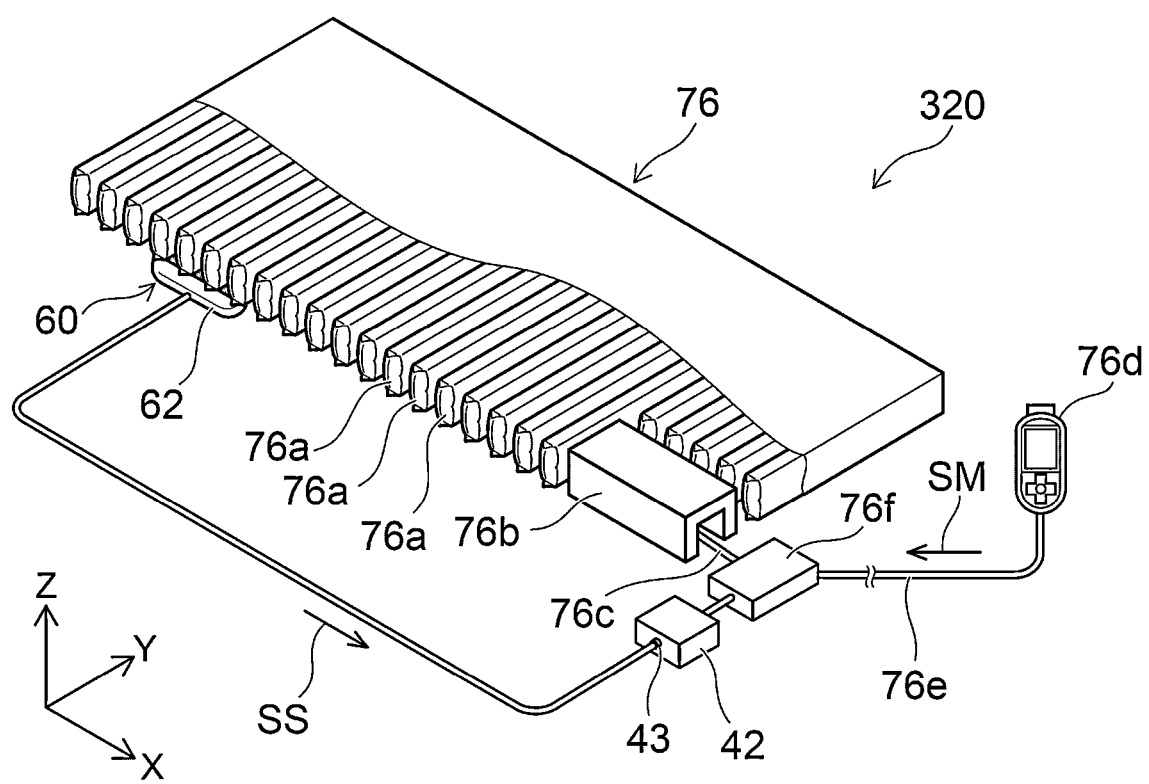
FIG. 6 is a schematic perspective view illustrating a motorized furniture according to a second embodiment of the present invention.

FIG. 6 is a schematic perspective view illustrating a motorized furniture according to a second embodiment of the present invention.

As illustrated in FIG. 6, a motorized furniture 320 according to this embodiment includes a mattress 76 and the control unit 42. The motorized furniture 320 may be further provided with the acquisition unit 43. The acquisition unit 43 may be included in the control unit 42. The mattress 76 may be placed on the section 71 of the motorized bed. Alternatively, a surface located below the mattress 76 may be a horizontal surface.

For example, the mattress 76 includes multiple air cells 76a. For example, the multiple air cells 76a are arranged in a direction that connects the head part of the mattress 76 with the foot part thereof (e.g. in the X-axis direction). For example, each of the multiple air cells 76a extends in the left-right direction of the mattress 76 (e.g. in the Y-axis direction). For example, the volume of air inside each of the multiple air cells 76a is controlled by a pump unit 76b. This changes the pressure inside each of the multiple air cells 76a. For example, this can change the height of each of the multiple air cells 76a (e.g. the position of the upper end of each of the multiple air cells in the Z-axis direction).

For example, a mattress driving unit 76f (e.g. an electrical circuit unit) is provided. The pump unit 76b is connected to the mattress driving unit 76f through a cable 76c. A control unit of the mattress driving unit 76f operates the pump unit 76b, thus making it possible to control the state of each of the multiple air cells 76a in various ways.

In this example, a mattress manipulation unit 76d is provided. The mattress manipulation unit 76d is connected to the mattress driving unit 76f through a cable 76e. The mattress manipulation unit 76d is configured to receive manipulation by a person such as the user of the mattress 76. A signal SM corresponding to the manipulation the mattress manipulation unit 76d has received is supplied to the mattress driving unit 76f, thus making it possible to manually control the state of the mattress 76 (e.g. the shape of each of the multiple air cells 76a).

In this embodiment, in addition to the manual control, the state (e.g. the shape) of the mattress 76 is controlled by automatic control performed by the control unit 42.

In the embodiment, the detection unit 60 (the sensor 62, for example) is provided. The detection unit 60 is provided below the mattress 76. The detection unit 60 is configured to detect a biological signal including the body movement of the user of the mattress 76. The detection unit 60 outputs a signal SS corresponding to the biological signal. The acquisition unit 43 acquires this signal SS. This signal SS is supplied to the control unit 42. In this example, the signal SS also includes information on at least one of the respiratory rate and heartbeat rate of the user. The signal SS may include information on at least one of motions of the arms, torso, and feet of the user. The signal SS may include information on the rolling over of the user. The signal SS may include a signal on the number of the rolling over of the user.

The control unit 42 is configured to control the state (e.g. the shape) of the mattress 76 according to the variation ΔS of the signal SS. This control is performed in such a way that the control unit controls the mattress driving unit 76f to control the pump unit 76b, for example. In this manner, the control unit 42 is capable of performing the automatic control based on the biological signal in addition to the manual control.

Hereinbelow, firstly, an example of the state of the mattress 76 is described.

Figure 7A:
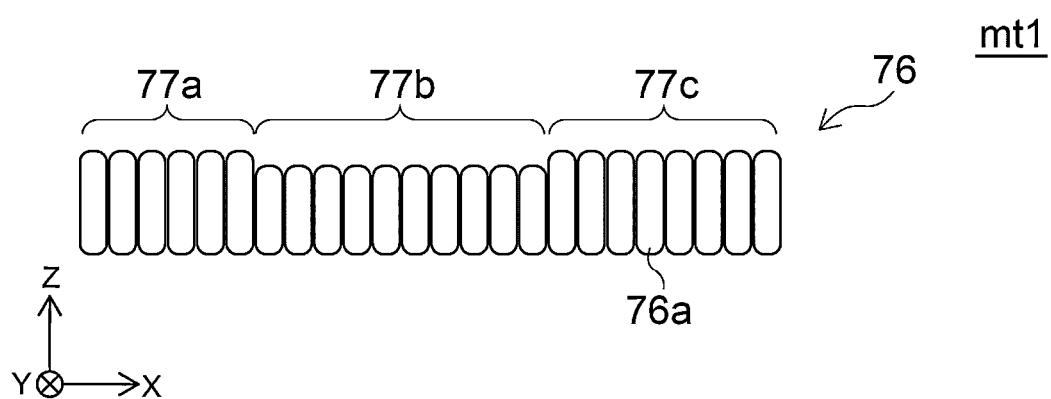
FIGS. 7A and 7B are schematic side views illustrating the motorized furniture according to the second embodiment.
Figure 7B:
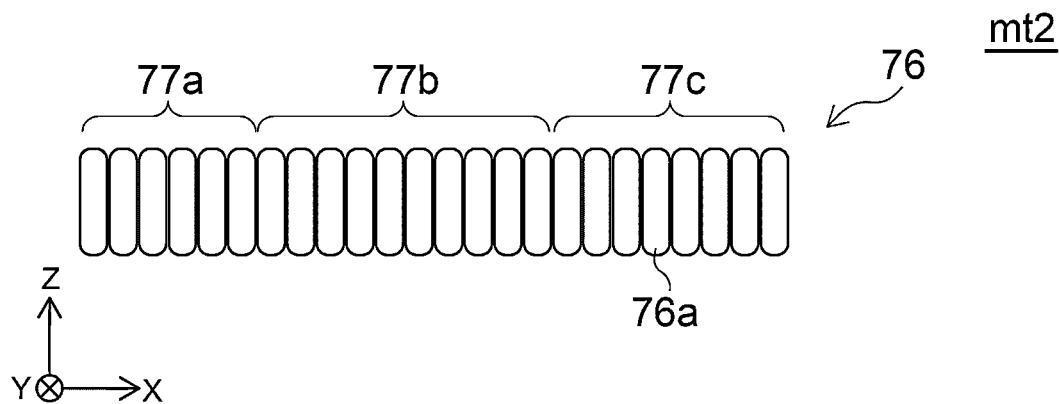

FIGS. 7A and 7B are schematic side views illustrating the motorized furniture according to the second embodiment.

These drawings illustrate the state (e.g. the shape) of the mattress 76. FIG. 7A corresponds to one state (a first mattress state mt1) of the mattress 76. FIG. 7B corresponds to another state (a second mattress state mt2) of the mattress 76.

A part of the multiple air cells 76a (a head part 77a) corresponds to the head part of the user. Another part of the multiple air cells 76a (a waist part 77b) corresponds to the waist part of the user. Still another part of the multiple air cells 76a (a foot part 77c) corresponds to the foot part of the user.

As illustrated in FIG. 7A, in the first mattress state mt1, the height (the height of the upper part) of the waist part 77b of the mattress 76 is low relative to the height (the height of the upper part) of the head part 77a of the mattress 76. For example, the height of the waist part 77b of the mattress 76 is lower than the height of the foot part 77c of the mattress 76. In the first mattress state mt1, the shape of the mattress 76 has a gentle inclination. When the user is laid on the mattress 76 in the first mattress state mt1, the back of the user becomes gently inclined. In the first mattress state mt1, the height of the foot part 77c may also be lower than the height of the head part 77a.

On the other hand, as illustrated in FIG. 7B, in the second mattress state mt2, the height of the waist part 77b of the mattress 76 is substantially the same as the height of the head part 77a of the mattress 76. The height of the waist part 77b of the mattress 76 is substantially the same as the height of the foot part 77c of the mattress 76. In the second mattress state mt2, the mattress 76 is substantially flat. When the user is laid on the mattress 76 in the second mattress state mt2, the back of the user turns substantially flat. In the second mattress state mt2, the height of the waist part 77b may be set slightly higher than the height of the head part 77a.

For example, it is assumed that the user can roll over easily when the mattress 76 is flat (e.g. in the second mattress state mt2). On the other hand, the user can fall asleep easily when the mattress 76 inclines gently (e.g. in the first mattress state mt1).

In the embodiment, the control unit 42 changes the shape of the mattress 76 based on the biological signal of the user. For example, the first mattress state mt1 and the second mattress state mt2 described above are switched each other. Thereby, it is possible to provide more comfortable sleep.

Figure 8A:
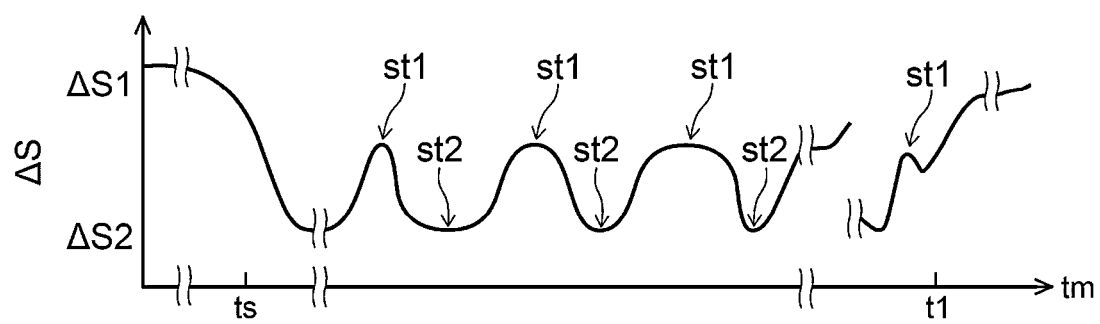
FIGS. 8A and 8B are schematic diagrams illustrating operations of the motorized furniture according to the second embodiment.
Figure 8B:
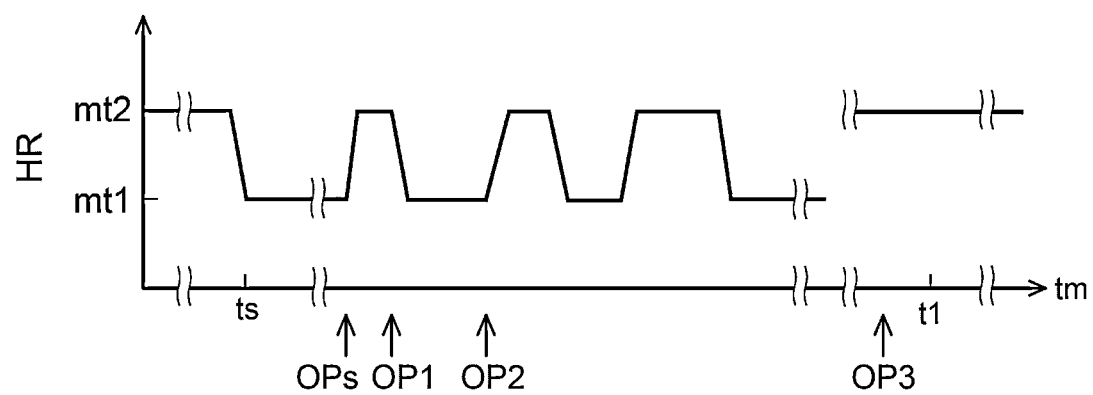

FIGS. 8A and 8B are schematic diagrams illustrating operations of the motorized furniture according to the second embodiment.

The horizontal axis of these drawings is time tm. The longitudinal axis of FIG. 8A indicates a variation ΔS of the signal SS. As illustrated in FIG. 8A, the signal SS includes multiple states (e.g. a first signal state st1 and a second signal state st2). In this case, the variation ΔS of the signal SS in the second signal state st2 is also smaller than the variation ΔS of the signal SS in the first signal state st1.

The longitudinal axis of FIG. 8B indicates a height HR of the waist part 77b of the mattress 76 relative to the height of the head part 77a of the mattress 76. In the first mattress state mt1, the waist part 77b is lower than the head part 77a, and the shape of the mattress 76 inclines gently. In the second mattress state mt2, the height of the waist part 77b is substantially the same as the height of the head part 77a, and the shape of the mattress 76 is flat.

The control unit 42 performs a first operation OP1 when the variation ΔS of the signal SS decreases. In the first operation OP1, the control unit decreases the height of the waist part 77b of the mattress 76 relative to the height of the head part 77a of the mattress 76. For example, the control unit 42 decreases the height of the waist part 77b when the variation ΔS of the signal SS tends to decrease after the peak (maximum) of the variation ΔS is over. For example, in the first operation OP1, the control unit controls the mattress so that the mattress transitions from the second mattress state mt2 to the first mattress state mt1. For example, in the first operation OP1, the control unit controls the shape of the mattress 76 so that the shape changes from a flat shape to a gently inclined shape, for example.

For example, the user's sleep is becoming deeper when the variation ΔS of the signal SS decreases. By controlling the shape of the mattress 76 so that the shape changes to a gently inclined shape at this stage, it is possible to help the user's deeper sleep. For example, this can make the user sleep deeply earlier. Thereby, it is possible to provide more comfortable sleep.

The control unit 42 may further perform a second operation OP2. The second operation OP2 is an operation performed when the variation ΔS of the signal SS increases. In the second operation OP2, the control unit 42 sets the height of the waist part 77b closer to the height of the head part 77a. For example, in the second operation OP2, the control unit 42 controls the mattress so that the mattress transitions from the first mattress state mt1 to the second mattress state mt2. For example, in the second operation OP2, the control unit controls the shape of the mattress 76 so that the shape changes from a gently inclined shape to a flat shape, for example. For example, the control unit 42 decreases the height of the waist part 77b when the variation ΔS of the signal SS tends to increase after the section (minimum) of the variation ΔS is over.

When the variation ΔS of the signal SS increases, the user often tries to roll over. By controlling the shape of the mattress 76 so that the shape changes from a gently inclined shape to a flat shape at this stage, it is possible to help the user roll over more easily and reduce the user's burden. Thereby, it is possible to provide more comfortable sleep.

Further, the control unit performs the first operation OP1 after the second operation OP2. This can help the user sleep deeply earlier after he/she rolls over, for example. The control unit iterates these first operation OP1 and second operation OP2. Thereby, it is possible to provide high-quality sleep.

The control unit 42 may further perform a third operation OP3 in addition to these first operation OP1 and second operation OP2. The third operation OP3 is an operation performed when the user gets up at predetermined time t1 (see FIG. 8A).

As has been described previously, the signal SS includes a first signal state st1 and a second signal state st2. For example, the first signal state st1 corresponds to REM sleep. The second signal state st2 corresponds to non-REM sleep. The control unit 42 performs the third operation OP3 when the signal SS becomes the first signal state st1 at the time before and closest to the predetermined time t1. In the third operation OP3, the control unit 42 keeps the state where the height of the waist part 77b is set closer to the height of the head part 77a (flat state).

For example, REM sleep occurs at the time before and closest to the predetermined time t1. Then, the control unit 42 keeps the flat state of the mattress 76 even when the variation ΔS of the signal SS decreases.

Thereby, the user can wake up comfortably. For example, when the user is in REM sleep at the time closest to the predetermined time t1, the user can wake up thanks to the flat state of the mattress 76.

In the third operation OP3, the control unit may change the shape of the mattress 76 to a reverse shape (a shape where the head part 77a is lower than the waist part 77b) according to the state (or taste) of the user. In this case, the head part of the user inclines below the torso. The shape of the mattress 76 in the third operation OP3 may be changed according to the state (such as the age, health conditions, and taste) of the user.

As illustrated in FIG. 8B, the control unit 42 may perform a falling asleep operation OPs. For example, at time ts, the user or the like makes an input indicating that the user wishes to fall asleep by manipulating the control device 160. For example, the mattress 76 is flat in a state before the time ts. When the falling asleep manipulation is made at the time ts, the control unit 42 sets the waist part 77b lower than the head part 77a. This helps the user fall asleep. Then, the control unit 42 performs the first operation OP1 and the second operation OP2 described above.

In the embodiment, for example, the control unit 42 may change the shape of the mattress 76, formed according to the variation ΔS of the signal SS, based on the relationship between past data on the variation ΔS of the signal SS and the shape of the mattress 76. For example, the control unit may change the shape of the mattress 76 in the first operation OP1 or the second operation OP2 based on the relationship between the past data on the variation ΔS of the signal SS and the shape of the mattress 76. For example, the shape of the mattress 76 that brings comfortable sleep sometimes differs from one user to another. In addition, the shape of the mattress 76 that brings comfortable sleep to each user sometimes differs between an initial period and later period of sleep. In this case, the control unit may change the shape of the mattress 76 to be set based on the relationship between the past data on the variation ΔS of the signal SS and the shape of the mattress 76. In other words, the control unit may set more appropriate shape of the mattress 76 by learning the relationship between the past data on the variation ΔS of the signal SS and the shape of the mattress.

In the above example, the heights of multiple portions of the mattress 76, which are located at different positions in the up-down direction thereof, are changed according to the variation ΔS of the signal SS corresponding to the biological signal. The up-down direction is a direction that connects the head part with the foot part, and corresponds to the X-axis direction of FIG. 6. For example, in the above example, the pressure inside the multiple portions of the mattress 76 (multiple air cells 76a), which are located at different positions in the up-down direction thereof, are changed according to the variation ΔS of the signal SS.

In the embodiment, the multiple air cells 76a may be arranged in the left-right direction (the Y-axis direction in FIG. 6). In the embodiment, the heights of multiple portions, which are located at different positions in the left-right direction, may be changed according to the variation ΔS of the signal SS corresponding to the biological signal. In the embodiment, the pressure inside the multiple portions (multiple air cells 76a), which are located at different positions in the left-right direction, may be changed according to the variation ΔS of the signal SS corresponding to the biological signal.

The motorized furniture 320 (see FIG. 6) according to this embodiment includes the control unit 42 capable of the above operations. The control unit 42 may include the above acquisition unit 43, or the acquisition unit 43 may be provided separately from the control unit 42. The motorized furniture 320 includes the controlled unit 70C (the movable unit 70, for example). The motorized furniture 320 may further include the above detection unit 60. An apneic state, snoring, or the like may be suppressed by the operations of the embodiment.

In the above example, the user's sleep state is presumed based on the biological signal, and the shape of the mattress 76 is controlled according to the sleep state. In the embodiment, the user's posture (such as a supine position, a prone position, or a lateral position) may be presumed. The shape of the mattress 76 may be controlled according to the presumption result of the user's posture.

In the above example, the shape of the mattress 76 is controlled based on the biological signal of the user. The stiffness of the mattress 76 may be controlled based on the biological signal of the user. At least one of the shape and stiffness of a pillow may be controlled based on the biological signal of the user. For example, the user has a taste in the shape or stiffness of the mattress 76. At least one of the shape and stiffness of the mattress 76 may be controlled according to this taste. For example, the user has a taste in the shape or stiffness of a pillow. At least one of the shape and stiffness of the pillow may be controlled according to this taste.

Hereinbelow, a description is given of an example of a flowchart of the motorized furniture according to this embodiment.

Figure 9:
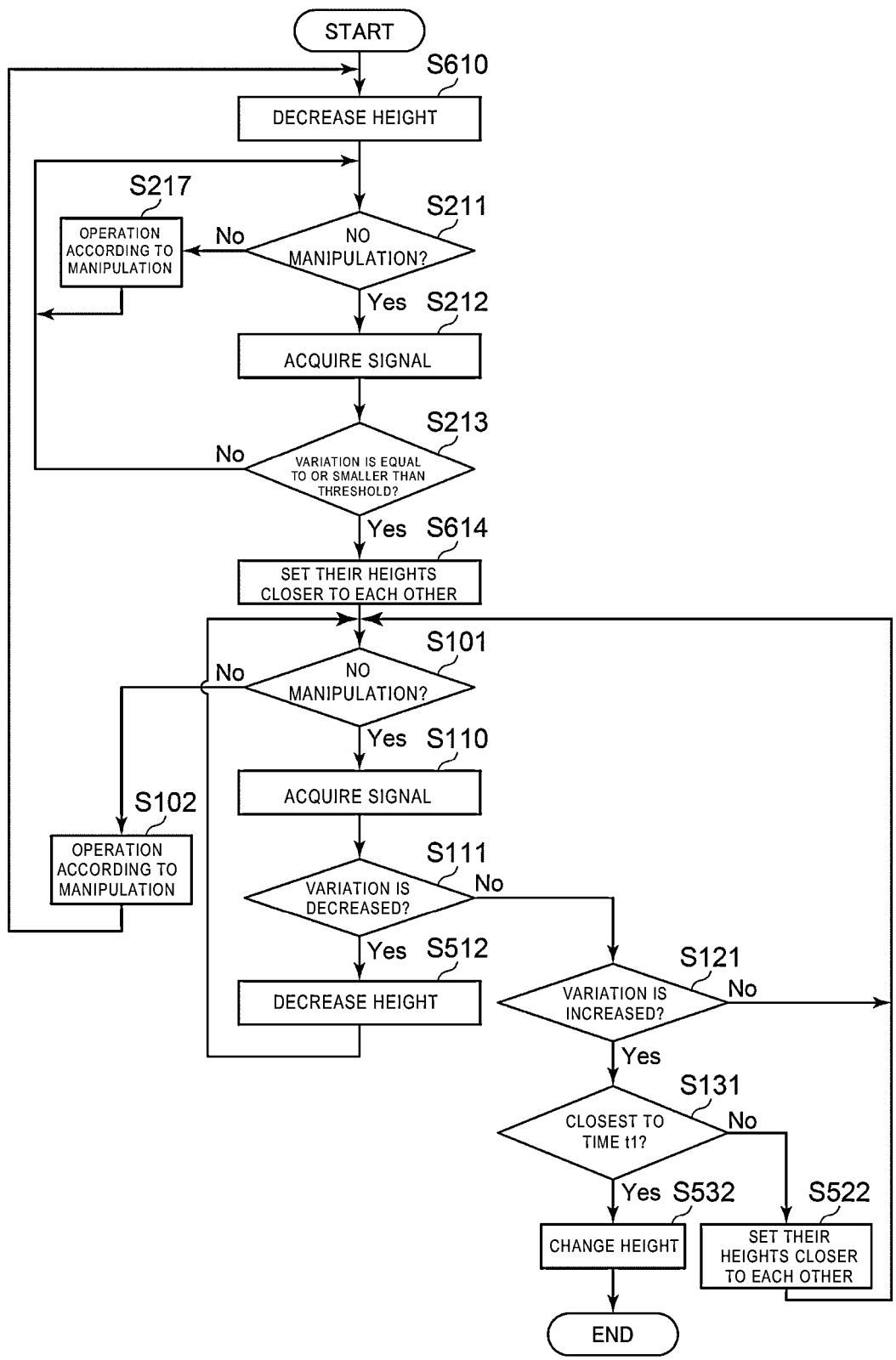
FIG. 9 is a flowchart illustrating the operations of the motorized furniture according to the second embodiment.

FIG. 9 is a flowchart illustrating the operations of the motorized furniture according to the second embodiment.

For example, an input indicating that the user wishes to fall asleep is made by manipulating the control device 160. Thereby, as illustrated in FIG. 9, the control unit decreases the height of the waist part 77b relative to that of the head part 77a (Step S610). For example, the control unit sets the height of the waist part 77b lower than that of the head part 77a.

Then, Steps S211 and S212 and Step S217 are executed. These steps are the same as steps described in relation to FIG. 5.

As illustrated in FIG. 9, it is judged whether or not the variation ΔS of the signal SS is equal to or smaller than a threshold (Step S213). If the variation ΔS of the signal SS is not equal to or smaller than the threshold, the process returns back to Step S211.

In Step S213, if it is judged that the variation ΔS is equal to or smaller than the threshold, the control unit sets the height of the waist part 77b closer to the height of the head part 77a (Step S614). For example, the control unit makes the mattress 76 substantially flat. Steps S213 and S614 described above correspond to the above falling asleep operation OPs, for example.

Then, Step S101 and Step S102 are executed. These steps are the same as steps described in relation to FIG. 5.

As illustrated in FIG. 9, the signal SS corresponding to the biological signal is acquired (Step S110). It is further judged whether or not the variation ΔS of the signal SS is decreased, for example (Step S111).

If the variation ΔS is decreased, the control unit decreases the height of the waist part 77b relative to that of the head part 77a (Step S512). For example, the mattress 76 turns substantially flat. Then, the process returns back to Step S101, for example. Step S111 and Step S512 correspond to the above first operation OP1. The first operation OP1 helps the user sleep.

In Step S111, if the variation ΔS is not decreased, it is judged whether or not the variation ΔS is increased (Step S121). Whether or not the variation ΔS is increased is judged using the threshold regarding the increase of the variation ΔS, for example.

In Step S121, if the variation ΔS is not increased, it means there is substantially no change in the variation ΔS. In this case, the process returns back to Step S101.

In Step S121, if the variation ΔS is increased (i.e. if in the first signal state st1 where the variation ΔS is large), it is judged whether or not this first signal state st1 is the first signal state st1 at the time before and closest to the predetermined time t1 (Step S131).

In Step S131, if this first signal state is not at the time closest to the time t1 (if "NO"), the control unit sets the height of the waist part 77b closer to the height of the head part 77a (Step S522). For example, the control unit makes the mattress 76 substantially flat. Then, the process returns back to Step S101, for example. Step S131 and Step S522 correspond to the above second operation OP2. The second operation OP2 helps the user roll over more easily, for example.

In Step S131, if it is judged that this first signal state st1 is the first signal state st1 at the time before and closest to the time t1, the control unit changes at least one of the height of the waist part 77b and the height of the head part 77a (Step S532). For example, the control unit makes the mattress 76 substantially flat. Alternatively, the control unit changes the shape of the mattress 76 to a reverse shape.

This helps the user wake up comfortably.

In this embodiment, some Steps may also be swapped each other within a technically possible range. For example, Step S111 and Step S121 may be swapped each other. In this case, Step S512 and Step S522 are also swapped in conjunction with this.

Third Embodiment

In this embodiment, the temperature of the motorized furniture is controlled based on the signal SS corresponding to the biological signal. For example, as has been described in relation to FIG. 1, the temperature control unit 73b (such as a heater) is sometimes provided as the controlled unit 70C. The temperature control unit 73b is provided at a position corresponding to the foot part of the user, for example. Hereinbelow, a description is given of an example of changing the temperature of the temperature control unit 73b based on the signal SS corresponding to the biological signal.

Figure 10A:
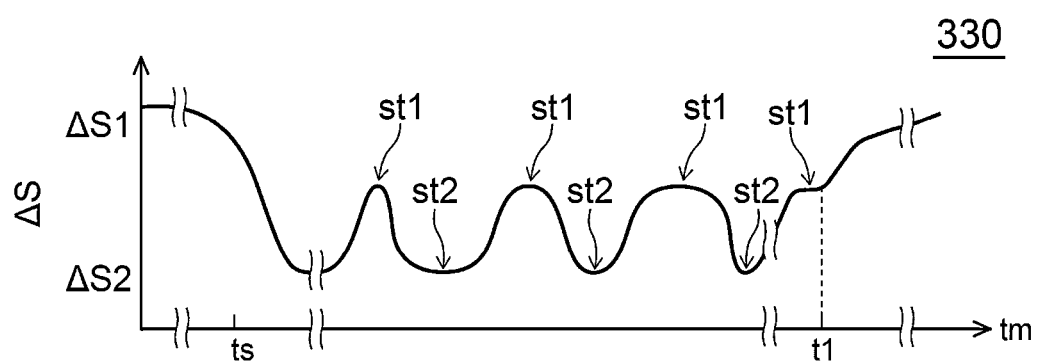
FIGS. 10A and 10B are schematic diagrams illustrating operations of a motorized furniture according to a third embodiment of the present invention.
Figure 10B:
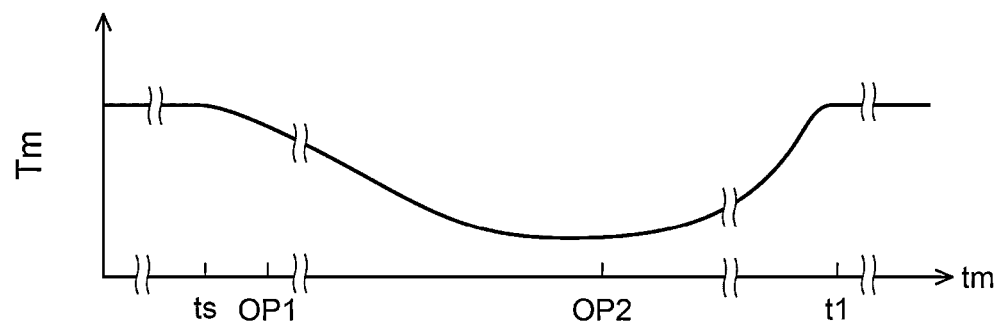

FIGS. 10A and 10B are schematic diagrams illustrating operations of the motorized furniture according to the third embodiment of the present invention.

The horizontal axis of these drawings is the time tm. The longitudinal axis of FIG. 10A indicates the variation ΔS of the signal SS. In this case, the signal SS also includes multiple states (e.g. a first signal state st1 and a second signal state st2). In this case, the variation ΔS of the signal SS in the second signal state st2 is also smaller than the variation ΔS of the signal SS in the first signal state st1.

The longitudinal axis of FIG. 10B is temperature Tm of the motorized furniture 320. In this example, the temperature Tm is the temperature of the temperature control unit 73b. The control unit 42 is configured to control the temperature Tm of the motorized furniture 320 according to the variation ΔS of the signal SS. The control unit 42 performs a first operation OP1. The first operation OP1 is an operation performed when the variation ΔS of the signal SS decreases. In the first operation OP1, the control unit 42 decreases the temperature Tm when the variation ΔS of the signal SS decreases.

For example, the temperature of the user observed when the user is sleeping is lower than the temperature of the user observed when the user is awake. By controlling the temperature of the motorized furniture according to the state of the user, it is possible to provide the user with more comfortable sleep.

The control unit 42 may further perform a second operation OP2. The second operation OP2 is an operation performed when sleep is becoming gradually shallower. For example, during one sleep period, a sleep state in a sleep start period and a sleep state in a period near the end of sleep sometimes differ from each other. For example, in the start period, the difference between the first signal state st1 (e.g. corresponding to REM sleep) and the second signal state st2 (e.g. corresponding to non-REM sleep) is assumed to be large. For example, in the period near the end, the difference between the first signal state st1 and the second signal state st2 is assumed to be smaller than the difference in the start period. For example, it is possible to presume a sleep state based on a change in the difference between the first signal state st1 and the second signal state st2.

For example, the control unit performs the second operation OP2 when the difference between the first signal state st1 and the second signal state st2 is smaller than a certain value (threshold). In the second operation OP2, for example, the control unit increases the temperature Tm of the motorized furniture 320 (the temperature control unit 73b, for example). Thereby, it is possible to provide the user with more comfortable sleep.

Besides, when the controlled unit 70C includes the lighting unit 73a (see FIG. 1), the control unit 42 may change the operation state (e.g. at least one of the lightness and color) of the lighting unit 73a based on the variation ΔS of the signal SS corresponding to the biological signal.

The control unit may control at least one of the lightness and color of a display unit (or a light) of the control device 160 based on the biological signal of the user. For example, the control unit may perform control such that the motorized furniture 310 emits a scent that helps the user sleep or wake up based on the biological signal of the user.

In the third embodiment, the signal SS also includes information on at least one of the respiratory rate and heartbeat rate of the user. The signal SS may include information on at least one of motions of the arms, torso, and feet of the user. The signal SS may include information on the rolling over of the user. The signal SS may include a signal on the number of the rolling over of the user.

Hereinbelow, some examples of the sensor 62 are described.

Figure 11A:
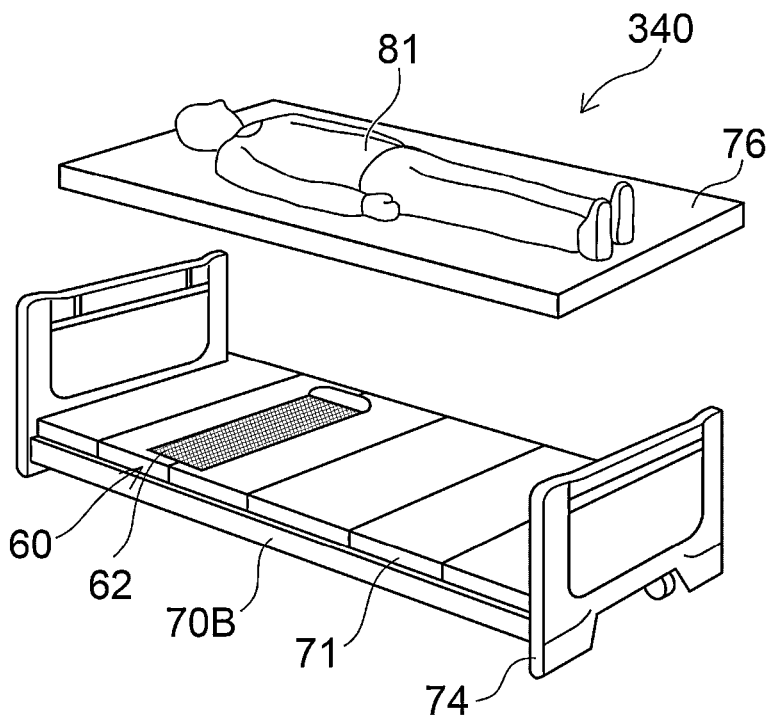
FIGS. 11A and 11B are schematic diagrams illustrating the motorized furniture according to the embodiments.
Figure 11B:
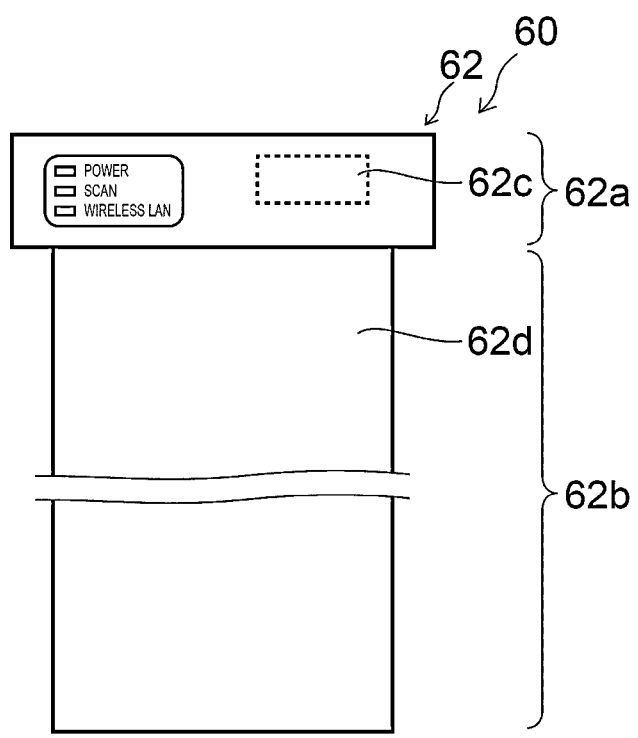

FIGS. 11A and 11B are schematic diagrams illustrating the motorized furniture according to the embodiments. FIG. 11A is a schematic perspective view illustrating the sensor 62 and the layout of the sensor 62. FIG. 11B is a schematic plan view illustrating the sensor 62. In FIG. 11A, constituents are drawn separately from each other for making the drawing easy to read and understand.

As illustrated in FIG. 11A, in a motorized furniture 340, the section 71 is provided on a bed leg part 74 of a bed part 70B. The mattress 76 is provided on the section 71. A user 81 lies on the mattress 76. The sensor 62 (the detection unit 60) is provided between the section 71 and the mattress 76, for example. In this example, the sensor 62 is in the shape of a sheet or plate.

As illustrated in FIG. 11B, the sensor 62 includes a circuit unit 62a and a sensor unit 62b. The circuit unit 62a includes a communication unit 62c. The communication unit 62c is configured to transmit and receive data to and from the control unit 42. They transmit and receive data by any method including at least one of wired and wireless communications.

The sensor unit 62b includes a sensor device 62d, for example. The sensor unit 62b is configured to detect a force (or characteristics corresponding to the force) received at the sensor unit 62b. The force includes at least one of pressure and sound wave, for example. The sensor unit 62b includes a pressure sensor, for example. The sensor unit 62b includes a microphone, for example.

The force (at least one of pressure and sound wave) charged by the user 81 is applied on the sensor unit 62b through the mattress 76. For example, a signal based on the force detected by the sensor unit 62b is output from the circuit unit 62a. The signal thus output is supplied to the control unit 42. The control unit 42 presumes the state of the user 81 (such as a state where the user is away from the bed, the user is sleeping, or the user wakes up) based on at least one of the magnitude of the signal (force) and a temporal change in the magnitude of the signal (force). Alternatively, the circuit unit 62a may presume the state of the user 81 (such as a state where the user is away from the bed, the user is sleeping, or the user wakes up) based on at least one of the force detected by the sensor 62b and a temporal change in the force. The state of the user 81 may include a state where the user gets up, the user is preparing for getting out of the bed (e.g. the user is in a sitting position with his/her soles of feet on the floor), the user is away from the bed, the user is falling asleep, the user is sleeping, or the user wakes up.

Further, at least one of the control unit 42 and the circuit unit 62a detects the biological signal of the user 81 based on at least one of the magnitude of the signal (force) and a temporal change in the magnitude of the signal (force). The biological signal includes at least one of the respiratory rate and heartbeat rate of the user. A sleep state may be presumed based on the biological signal. The posture of the user 81 during sleep may be presumed based on the biological signal.

For example, vibrations according to the state of the user 81 are applied on the sensor unit 62b. The vibrations correspond to the body movement of the user 81, for example. The sensor unit 62b detects the vibrations. The vibrations may include sound.

For example, vibration detection means (the sensor unit 62b) and a processing unit (at least a part of at least one of the circuit unit 62a and the control unit 42) are arranged. The processing unit includes a computer, for example. The vibration detection means is configured to detect vibrations of a sleeper (the user 81) on bedding (the bed part 70B), for example. The processing unit includes amount of activity calculation means, sleep judgment value calculation means, and sleep state judgment means. These means are functionally separated from each other. The amount of activity calculation means is configured to calculate the amount of activity of the sleeper per sampling unit time based on the vibrations detected by the vibration detection means. For example, the sleep judgment value calculation means is configured to calculate, as a sleep judgment value, the total sum of values that are obtained by respectively multiplying the amount of activity at first time (e.g. the current time) and the amount of activity calculated at second time (e.g. the time prior to the current time) by their modification coefficients each obtained by weighting according to the corresponding time. For example, the sleep state judgment means is configured to judge that the user is awake if the sleep judgment value exceeds a predetermined threshold, and judge that the user is sleeping if the sleep judgment value is equal to or smaller than the predetermined threshold.

FIGS. 12A to 12D are schematic diagrams illustrating another motorized furniture according to the embodiments.

Figure 12A:
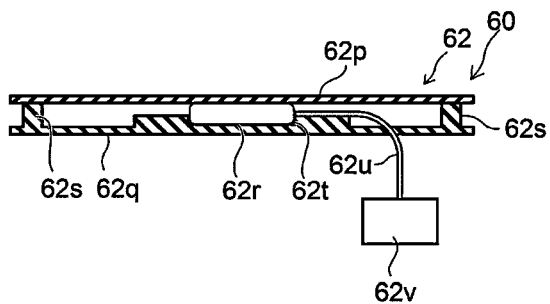
FIGS. 12A to 12D are schematic diagrams illustrating another motorized furniture according to the embodiments.
Figure 12B:
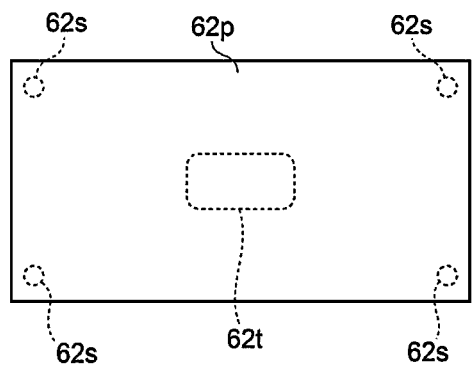
Figure 12C:
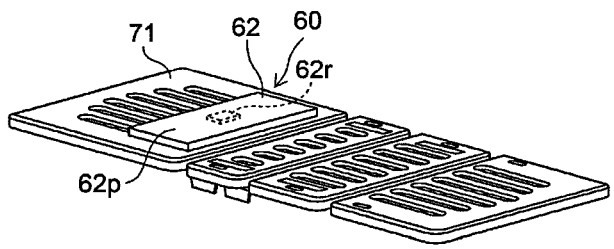
Figure 12D:
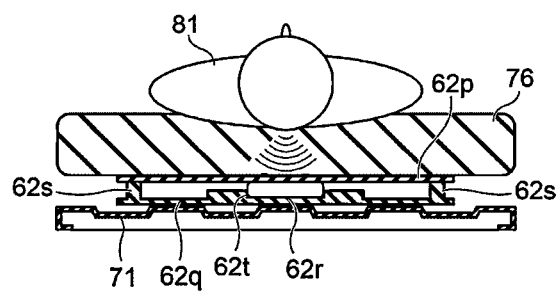

FIG. 12A is a sectional view of an example of the sensor 62. FIG. 12B is a plan view of the example of the sensor 62. FIG. 12C is a perspective view illustrating the layout of the sensor 62. FIG. 12D is a side view illustrating the layout of the sensor 62.

As illustrated in FIG. 12A, in this example, the sensor 62 includes a first platy body 62p and a second platy body 62q. The second platy body 62q is opposed to the first platy body 62p. These platy bodies may be sheet shaped.

The second platy body 62q includes support protrusions 62s. The support protrusions 62s are opposed to an outer edge part of the first platy body 62q. The first platy body 62p includes an inner part located inside the outer edge part. An air housing body 62r is provided between the inner part and the second platy body 62q. In this example, a groove 62t is provided in the second platy body 62q. The air housing body 62r is provided in the space formed by (the space divided by) the groove 62t. One end of a signal line 62u is connected to the air housing body 62r. The other end of the signal line 62u is connected to a detection circuit 62v (detection device).

As illustrated in FIG. 12B, the support protrusions 62s are opposed to a part of the outer edge of the first platy body 62p. In this example, the support protrusions 62s are arranged at four corner parts of the first platy body 62p. The sensor 62 is in the shape of a sheet or plate.

As illustrated in FIG. 12C, the above sensor 62 is placed on the section 71. As illustrated in FIG. 12D, the sensor 62 is placed on the section 71, and the mattress 76 is placed on the sensor. The user 81 lies on the mattress 76.

For example, a force corresponding to the body movement of the user 81 is applied on the air housing body 62r. This force includes vibrations, for example. The force (or the characteristics corresponding to the force) applied on the air housing body 62r is detected by the detection circuit 62v. For example, the air housing body 62r is provided with a pressure detector, and a signal (detection result) acquired by the pressure detector is supplied to the detection circuit 62v. For example, the air housing body 62r is provided with a microphone, and a signal (detection result) acquired by the microphone is supplied to the detection circuit 62v. For example, an output (signal) from the detection circuit 62v is supplied to the control unit 42. The control unit 42 presumes the state of the user 81 (such as a state where the user is away from the bed, the user is sleeping, or the user wakes up). Alternatively, the detection circuit 62v may presume the state of the user 81 (such as a state where the user is away from the bed, the user is sleeping, or the user wakes up) based on at least one of the detected force and a temporal change in the force. The state of the user 81 may include a state where the user gets up, the user is in a sitting position with his/her soles of feet on the floor (e.g. the user is preparing for getting out of the bed), the user is away from the bed, the user is falling asleep, the user is sleeping, or the user wakes up.

The sensor 62 is a biological information collection device, for example. In the sensor 62, the first platy body 62p is disposed on the side close to the body of the user 81, for example. The second platy body 62q is provided on the support side, for example. The deformable air housing body 62r for detecting the air pressure is provided between central parts of the first platy body 62p and the second platy body 62q. The groove 62t for mounting the air housing body 62r therein is provided in the central part of the second platy body 62q. The support protrusions 62s protrude in the direction from the second platy body 62q toward the first platy body 62p. The support protrusions 62s support the circumferential four corners of the first platy body 62p. The support protrusions 62s constantly support the first platy body 62p to keep it in a horizontal state (normal state), for example.

In the embodiments, various modifications of the sensor 62 are possible.

In the embodiments, the control unit 42 may control, as the controlled unit 70C, at least one of the lighting unit 73a and the temperature control unit 73b (see FIG. 1) based on the state of the user 81 detected by the detection unit 60.

For example, the control unit may change the lightness (e.g. including on/off) of the lighting unit 73a based on the state (at least one of states where the user gets up, the user is in a sitting position with his/her soles of feet on the floor (e.g. the user is preparing for getting out of the bed), the user is away from the bed, the user is falling asleep, the user is sleeping, and the user wakes up) of the user 81 detected by the sensor 62. For example, the control unit may change the direction of light, emitted from the lighting unit 73a, based on the state of the user 81 detected by the sensor 62. The lighting unit 73a includes at least one of ceiling light, reading light, and foot light, for example. The lighting unit 73a includes any light of the room the user 81 is in. For example, the control unit controls the lighting unit 73a when the variation of the signal SS (detection signal) decreases. For example, the control unit may turn down the lighting unit 73a when the variation of the signal SS (detection signal) decreases. This makes it possible to provide a motorized furniture capable of facilitating ease of use, and makes it possible to provide a motorized furniture capable of offering more comfortable sleep.

For example, the control unit may change the temperature (e.g. including on/off) of the temperature control unit 73b based on the state of the user 81 detected by the sensor 62. The temperature control unit 73b may control the temperature around the motorized furniture (e.g. the temperature of the room the user 81 is in), for example. This makes it possible to provide a motorized furniture capable of facilitating ease of use, and makes it possible to provide a motorized furniture capable of offering more comfortable sleep.

Figure 13:
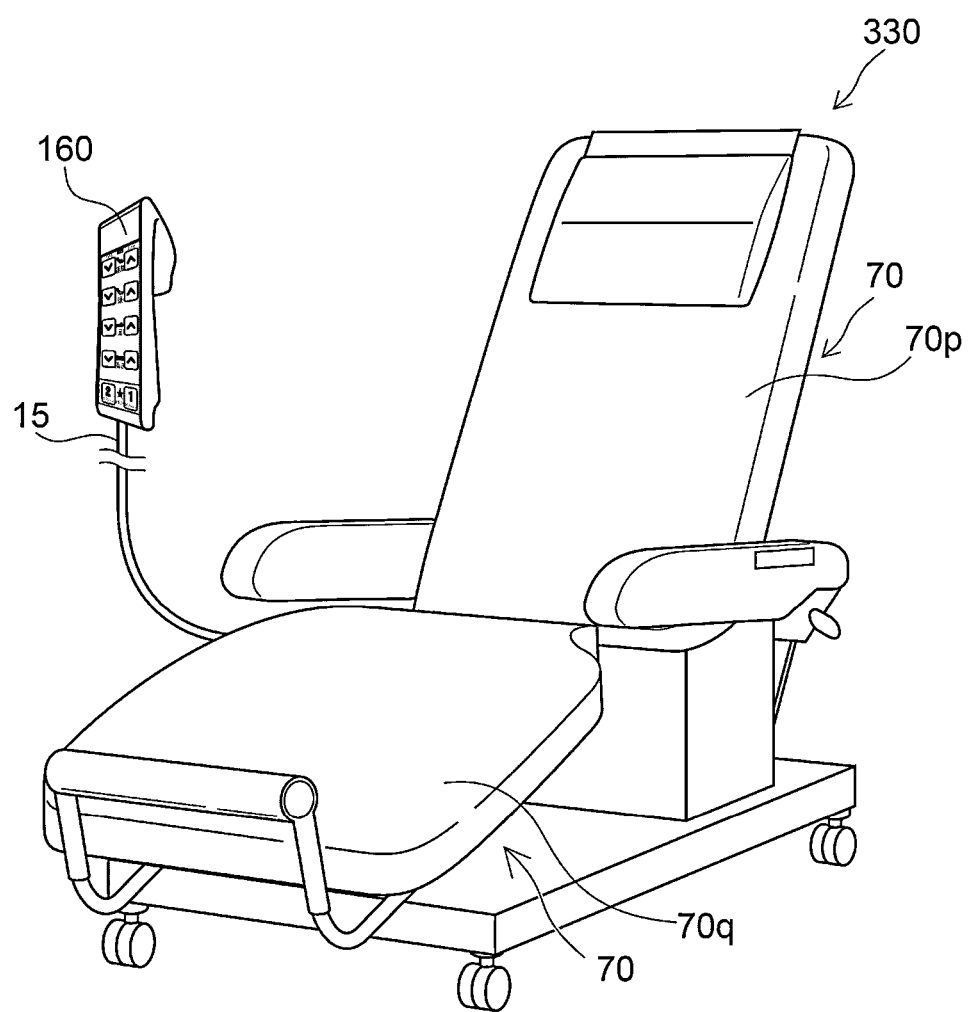
FIG. 13 is a schematic perspective view illustrating a motorized furniture according to another embodiment of the present invention.

FIG. 13 is a schematic perspective view illustrating a motorized furniture according to another embodiment of the present invention.

As illustrated in FIG. 13, a motorized furniture 330 is a motorized chair. The motorized furniture 330 includes the movable unit 70. The movable unit 70 includes a backrest part 70p and a seating face part 70q. The backrest part 70p corresponds to a section part capable of changing its angle. The seating face part 70q corresponds to a height change part. The seating face part 70q may be capable of changing its angle. The control device 160 according to the embodiments control these parts of the movable unit 70. In the motorized furniture 330, the movable unit 70 also moves according to the state of the user 81.

In the embodiments, in the case where the movable unit 70 is provided, a drive device of the movable unit 70 (such as a motor) is preferably provided on the foot side of the motorized furniture. This makes sound generated by the operation of the drive device less likely to reach the head part of the user 81, and thereby makes the user more comfortable. In the embodiments, the movement speed of the movable unit 70 in the case of the automatic control may be slower than the movement speed of the movable unit 70 in the case of the manual control. This makes the user 81 less likely to feel a sense of discomfort. For example, the user 81 becomes less likely to be woken up by the movement of the movable unit 70 by the automatic control.

In the embodiments, the state of the user 81 may include a state where the user gets up, the user is preparing for getting out of the bed (e.g. the user is in a sitting position with his/her soles of feet on the floor), the user is away from the bed, the user is falling asleep, the user is sleeping, the user wakes up, or the user rises from the bed.

In FIG. 5 and FIG. 9, the signal SS corresponding to the biological signal may be acquired (Step S212) before the judgment on whether or not manipulation is performed (Step S211). For example, the process may proceed in such a way that the signal SS is acquired periodically, and the process proceeds to and after Step S213 according to the result in Step S211.

When the section angle θ is equal to or larger than 3 degrees and smaller than 12 degrees, it is effective in the treatment of orthostatic hypotension, for example. For example, it is reported that the back raised state makes an airway less likely to be obstructed than the horizontal supine position, and thus sleeping in the back raised state improves respiratory conditions during sleep with regard to obstructive sleep apnea syndrome.

For example, it is assumed that the user can roll over easily when the upper surface of the section 71 (bed) is flat (the first angle θ1, for example). On the other hand, it is assumed that, when the section 71 (the back section 70a) inclines gently (the second angle θ2, for example), the user 81 finds it easy to breathe and easy to relax since the parasympathetic nerve becomes predominant, and thereby the user 81 can fall asleep easily.

As described above, in the first embodiment, in the first operation OP1, the control unit increases the section angle θ from the first angle θ1 to the second angle θ2 when the variation ΔS of the signal SS decreases, for example. This makes it possible to improve the respiratory conditions of the user 81 during sleep, for example. This makes it possible to prevent the user 81 from becoming apneic and waking up during sleep, for example. Thereby, it is possible to provide more comfortable sleep.

In the first embodiment, the control unit performs the first operation OP1 after the second operation OP2, for example. This makes it possible to prevent the user 81 from becoming apneic after he/she rolls over and waking up during sleep, for example. The control unit iterates these first operation OP1 and second operation OP2. Thereby, it is possible to provide high-quality sleep.

As described above, in the second embodiment, the control unit controls the shape of the mattress 76 so that the shape changes to a gently inclined shape when the variation ΔS of the signal SS decreases, for example. This makes it possible to improve the respiratory conditions of the user 81 during sleep, for example. This makes it possible to prevent the user 81 from becoming apneic and waking up during sleep, for example. Thereby, it is possible to provide more comfortable sleep.

In the second embodiment, the control unit performs the first operation OP1 after the second operation OP2, for example. This makes it possible to prevent the user 81 from becoming apneic after he/she rolls over and waking up during sleep, for example. The control unit iterates these first operation OP1 and second operation OP2. Thereby, it is possible to provide high-quality sleep.

As has been described in the above embodiments, the inclination of the section 71 may be the section angle θ. As has been described, the inclination of the section 71 may be an inclination relative to the frame 75 of the bed, or may be an angle relative to the floor surface. For example, the inclination of the section 71 may be changed by inclining the frame 75 relative to the floor surface. The inclination of the section 71 may be an inclination including the inclination of the section 71 relative to the frame 75 and the inclination of the frame 75 relative to the floor surface.

In one example of the embodiments, the control unit 42 performs the first operation OP1 when the variation ΔS of the signal SS decreases. In the first operation OP1 or the second operation OP2, the control unit 42 decreases the height of the waist part 77b of the mattress 76 relative to the height of the head part 77a of the mattress 76. As has been described, the height of each of the multiple air cells 76a of the mattress 76 can be changed by changing the pressure inside the corresponding one of the multiple air cells 76a. Accordingly, this first operation OP1 may include decreasing the difference between the pressure in the head part 77a and the pressure in the waist part 77b.

As has been described, the signal SS corresponds to at least one of the respiratory rate, the heartbeat rate, and the body movement. The variation ΔS of the signal SS may correspond to at least one of the respiratory rate, the heartbeat rate, and the body movement. The pulse rate may be deemed as substantially the same as the heartbeat rate.

Hereinbelow, an example of the falling asleep operation Ops (FIG. 4B, for example) is described.

In one example, the user 81 or the like makes an input indicating that the user wishes to fall asleep by manipulating the control device 160. The user 81 or the like includes the user 81 of the motorized furniture 310, 320, 330, or 340 and the carer of the user, for example. For example, the control device 160 may include a reception button or the like for transition to the falling asleep judgment operation. As has been described, the control device 160 can be connected to the control unit 42 by any method such as wired or wireless communication. The control device 160 may be a "smartphone type", for example.

The control device 160 may include a touch panel type input unit (such as the manipulation reception unit 20), for example. For example, an input area for transition to a "falling asleep mode" may be provided in a display unit of the touch panel. The user 81 "touches" this input area to transition to the falling asleep judgment operation. If "falling asleep" is judged in the falling asleep judgment operation, the control unit 42 performs the falling asleep operation Ops. In the above example, the time when an input indicating that the user wishes to fall asleep is made corresponds to the time ts (see FIG. 4B).

In another example, the falling asleep operation Ops may start at the preset time. For example, a time switch is set. For example, specific time is set, and the control unit 42 transitions to the falling asleep judgment operation at this time without manipulation of the user 81 or the like. In this case, the control unit 42 also performs the falling asleep operation Ops if "falling asleep" is judged in the falling asleep judgment operation. In this example, the preset specific time corresponds to the time ts (see FIG. 4B). The specific time is set by the user 81 or the like, for example.

Hereinbelow, a description is given of some examples of the "falling asleep mode" including "sleep" judgment, the falling asleep operation Ops, and the like.

Figure 14:
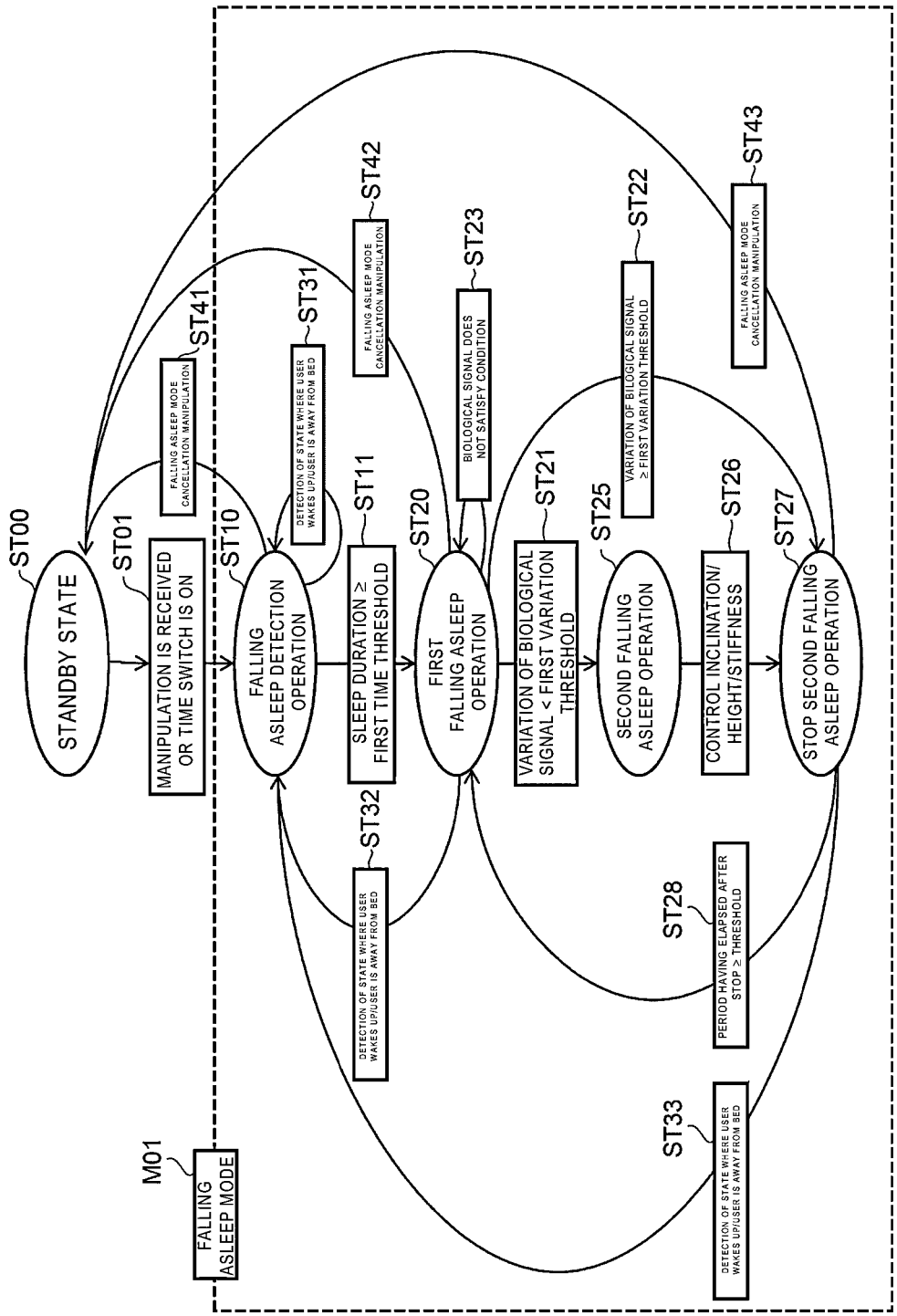
FIG. 14 is a schematic diagram illustrating operations of the motorized furniture according to the embodiments.

FIG. 14 is a schematic diagram illustrating operations of the motorized furniture according to the embodiments.

Figure 15:
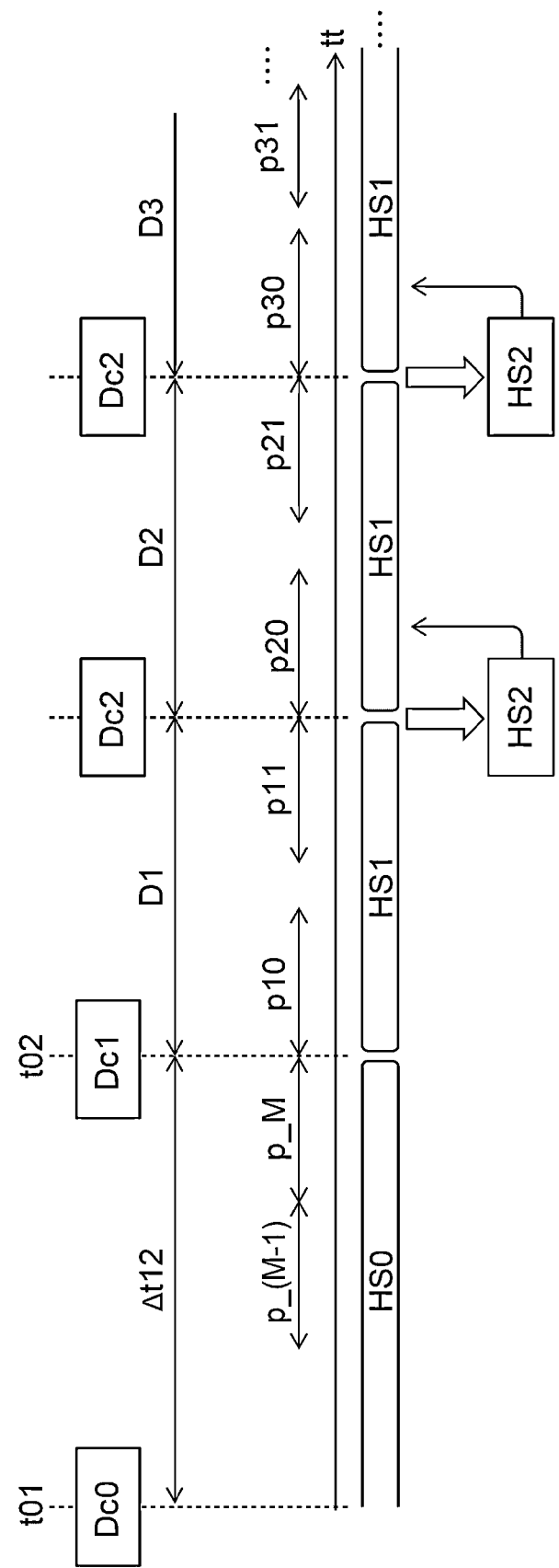
FIG. 15 is another schematic diagram illustrating the operations of the motorized furniture according to the embodiments.

FIG. 15 is another schematic diagram illustrating the operations of the motorized furniture according to the embodiments.

In FIG. 15, the horizontal axis is time tt.

As illustrated in FIG. 14, the control device 160 (or the control unit 42) has a standby state (Step ST00), for example. In response to manipulation received by the manipulation reception unit 20 or by way of the time switch, the control unit 42 transitions to a falling asleep mode M01 (Step ST01).

When the control unit 42 transitions to the falling asleep mode M01, the control unit performs a falling asleep detection operation HS0 (see FIG. 15) (Step ST10). In the falling asleep detection operation HS0, the control unit 42 detects the user 81's sleep start. In one example, the control unit 42 acquires the signal SS from the detection unit 60 (such as the sensor 62)(the signal corresponding to the biological signal of the user 81) to detect the user 81's sleep. In another example, the control unit 42 may acquire "a signal indicating that the user 81 is sleeping" detected by the detection unit 60 (such as the sensor 62). For example, it is judged that the user is "sleeping" if the variation ΔS of the signal SS corresponding to the biological signal (such as the respiratory rate and heartbeat rate) is smaller than the threshold. As has been described, the variation ΔS may include at least one of a temporal change in the signal SS and a change in the amplitude of the signal SS, for example. The biological signal may include information on the body movement of the user 81. The biological signal may include a signal on the rolling over of the user (such as information on the user's posture during sleep). The falling asleep detection operation HS0 is, for example, a "sleep detection waiting state". The falling asleep detection operation HS0 corresponds to Step S212 and Step S213, for example (see FIG. 5 and FIG. 9).

In the falling asleep detection operation HS0, assume that the time when it is judged that "the user 81 is sleeping" is first time t01 (see FIG. 15). As illustrated in FIG. 15, the control unit 42 (or the detection unit 60) performs a judgment operation Dc0 to judge whether or not the user 81 is sleeping. The time when it is judged that "the user 81 is sleeping" corresponds to the first time t01. The first time t01 is the time when the sleep of the user 81 of the motorized furniture is detected.

As illustrated in FIG. 14, for example, the control unit 42 measures the elapse of time since the first time t01 ("sleep duration"). The "sleep duration" denotes a period of time in which sleep continues. If the "sleep duration" becomes equal to or larger than a first time threshold (Step ST11), the control unit 42 transitions to a first falling asleep operation HS1 (see FIG. 15)(Step ST20). This transition time is set at second time t02 (see FIG. 15). The first time threshold is 20 minutes, for example. The first time threshold may take any value exceeding 0 minute and equal to or smaller than 120 minutes.

For example, as illustrated in FIG. 15, the control unit 42 performs a judgment operation Dc1 at the second time t02. The time when it is judged that "the elapse of time Δt12 since the first time t01 is equal to or larger than the first time threshold" in the judgment operation Dc1 corresponds to the second time t02. The second time t02 corresponds to the time of transition from the falling asleep detection operation HS0 to the first falling asleep operation HS1.

The first falling asleep operation HS1 performed by the control unit 42 is the operation (e.g. monitor operation) of acquiring the signal SS corresponding to the biological signal of the user 81, for example.

As illustrated in FIG. 14, if the variation of the biological signal satisfies a predetermined condition (first variation condition)(Step ST21), the control unit 42 performs a second falling asleep operation HS2 (see FIG. 15)(Step ST25).

For example, as illustrated in FIG. 15, a predetermined period D1 elapses after the second time t02. When the predetermined period D1 elapses, the control unit 42 performs a judgment operation Dc2. The predetermined period D1 is 60 seconds, for example. In the judgment operation Dc2, it is judged whether or not the variation ΔS of the signal SS corresponding to the biological signal of the user 81 in a first period p11 during the first falling asleep operation HS1 satisfies the first variation condition. The variation ΔS of the signal SS in the first period p11 during the first falling asleep operation HS1 satisfies the first variation condition if this variation ΔS satisfies at least one of conditions where the variation ΔS in the first period p11 is smaller than the variation ΔS in a first prior period p10 prior to the first period p11 during the first falling asleep operation HS1, where the absolute value of the difference between the variation ΔS in the first period p11 and the variation ΔS in the first prior period p10 is smaller than a first variation threshold, and where the absolute value of the difference between the variation ΔS in the first period p11 and the variation ΔS in a period p_M prior to this period is smaller than the first variation threshold. The control unit performs the second falling asleep operation HS2 (see FIG. 15) if the variation ΔS satisfies this first variation condition (Step ST25 in FIG. 14). In one example, the variation ΔS is a heartbeat rate. The heartbeat rate may be a heartbeat rate per minute that is calculated from an average value of the number of heartbeats (the number of peaks R represented in a waveform in an electrocardiogram) in a certain period (e.g. 5 seconds), for example. In the embodiments, the heartbeat rate may be obtained by averaging the number of heartbeats in a period between peaks (between R-R) of the waveform.

In one example, the length of each of the first period p11 and the first prior period p10 may be equal to or longer than 10 seconds and equal to or shorter than 5 minutes.

In the above example, in the judgment of operation (Step ST21) on whether or not the variation of the biological signal satisfies the predetermined condition (first variation condition), the control unit evaluates the variation ΔS of the signal SS between the first period p11 and the period prior to the first period p11 during the first falling asleep operation HS1. As will be described later, the way of judgment using the first variation condition may be modified in various ways. As will be described later, the control unit may make judgments according to the result of evaluation of the variation ΔS of the signal SS in the first period p11 during the first falling asleep operation HS1. Then, if the variation of the biological signal satisfies the predetermined condition described above (first variation condition)(Step ST21), the control unit performs the second falling asleep operation HS2.

In the second falling asleep operation HS2, the control unit 42 performs at least one of: the operation of decreasing the inclination of the section 71 of the motorized furniture; the operation of decreasing the gap between the height of the head part 77a of the mattress 76 of the motorized furniture and the height of the waist part 77b of the mattress; and the operation of decreasing the difference between the pressure in the head part 77a and the pressure in the waist part 77b (Step ST26 in FIG. 14).

In Step ST26, the operations such as decreasing the inclination by a predetermined amount and decreasing the difference by a predetermined amount are performed. After Step ST26 is over, the control unit stops the second falling asleep operation HS2 (Step ST27 in FIG. 14).

In this manner, in the embodiments, for example, the control unit 42 performs the second falling asleep operation HS2 if the variation ΔS satisfies the first variation condition described above in the first falling asleep operation HS1. In the second falling asleep operation HS2, the control unit 42 decreases the inclination at the user 81's back, for example. Thereby, the user 81's posture turns close to flat, whereby the user finds it easy to roll over.

As illustrated in FIG. 14, if the variation ΔS does not satisfy the first variation condition described above (Step ST22) in the first falling asleep operation HS1, the process proceeds to Step ST27 and the control unit does not perform the second falling asleep operation HS2 (Steps ST25 and ST26). For example, the control unit 42 does not perform the second falling asleep operation HS2 if, in the first falling asleep operation HS1, the absolute value (difference value) of the difference between the variations ΔS described above exceeds the first variation threshold and the variation ΔS in the first period p11 is larger than the variation ΔS in the first prior period p10.

If the variation ΔS satisfies the first variation condition described above in the first falling asleep operation HS1 (Step ST21), the user 81's sleep is presumed to deep, for example. On the other hand, if the variation ΔS does not satisfy the first variation condition described above in the first falling asleep operation HS1 (e.g. Step ST22), the user 81's sleep is presumed to shallow. By performing the second falling asleep operation HS2 described above when the user 81's sleep is presumed to deep, it is possible to inhibit the user 81 from being woken up by the second falling asleep operation HS2.

In one example according to the embodiments, the control unit may perform the above control operation (such as the second falling asleep operation HS2) when the section angle θ in the falling asleep detection operation (Step ST10) is equal to or larger than 0 degree and equal to or smaller than 30 degrees. For example, if the section angle θ in the falling asleep detection operation (ST10) is smaller than 0 degree (negative angle) or larger than 30 degrees, the control unit may perform no control operation (such as the second falling asleep operation HS2) even when the process proceeds to the falling asleep mode M01. By not performing the control operation (such as the second falling asleep operation HS2) when the section angle θ takes the above angle, it is possible to reduce a sense of discomfort.

As illustrated in FIG. 14, if the detected signal SS does not satisfy the predetermined condition in the first falling asleep operation HS1 (Step ST23), the control unit may continue the first falling asleep operation HS1 (Step ST20). For example, when the signal SS is the heartbeat rate, an average heartbeat rate is calculated from three successive heartbeats. For example, in Step ST23, the process returns back to Step ST20 if the detected number of heartbeats is two or smaller. For example, the process may return back to Step ST20 if the average heartbeat rate thus detected does not fall within a predetermined range. For example, the process may return back to Step ST20 if the average heartbeat rate thus detected is smaller than 40 times/minute or larger than 100 times/minute.

On the other hand, for example, in Step ST21, the control unit transitions to the second falling asleep operation HS2 (Step ST25) if the difference between the average heartbeat rate in the first period p11 (see FIG. 15) and the average heartbeat rate in the first prior period p10 (see FIG. 15) is smaller than 5 times/minute. In this case, the first variation threshold is 5 times/minute.

In the embodiments, for example, the inclination angle decreased at a time is set small. For example, the difference between the angle of the section 71 (e.g. the section angle θ) after the decrease of inclination and the angle of the section 71 (the section angle θ) in the period prior to this period is 1 degree or smaller. This angle difference may be 0.6 degrees or smaller. This angle difference may be 0.3 degrees or smaller.

For example, during one change of the section angle θ, the change speed of the section angle θ in an "initial period" may be lower than the change speed of the section angle θ in a "later period" after this "initial period". For example, during one change of the section angle θ, the change speed of the section angle θ in the "later period" may be higher than the change speed of the section angle θ in a "further later period". The operation may be performed slowly at the start of the operation and the end of the operation.

In one example, a period of time needed from Step ST25 to Step ST27 is equal to or longer than 1 second and equal to or shorter than 3 seconds.

The control unit stops the control operation once one second falling asleep operation HS2 (the control operation such as the decrease of inclination) is over (Step ST27). When a threshold period (such as 60 seconds) elapses after this stop (Step ST28), the process returns back to the first falling asleep operation HS1 (Step ST20). For example, the control unit performs the second round's first falling asleep operation HS1 (Step ST20).

During one cycle (Steps ST20 to ST27), the user 81's sleep state is detected in Steps ST21 to ST23. Then, when the user 81's sleep is presumed to deep, the control unit performs the second falling asleep operation HS2 (the control operation such as the decrease of inclination)(Steps ST25 and ST26). The degree of control (such as the degree of the decrease of inclination) in one control operation is set small. The cycle as described above is iterated. In other words, as illustrated in FIG. 15, the control unit may iterate the first falling asleep operation HS1 and the second falling asleep operation HS2. An example of iteration of the first falling asleep operation HS1 and the second falling asleep operation HS2 will be described later.

For example, by the iteration of the above Steps ST20 to ST27, the section 71 turns flat, or the mattress 76 turns flat. When the section 71 turns flat or the mattress 76 turns flat, the change of the inclination, height, or stiffness reaches its limit and becomes no longer available. In this case, the process may return back to the standby state (Step ST00).

In the embodiments, the process may return back to the standby state (Step ST00) upon receipt of manipulation for cancelling the falling asleep mode M01 (Step ST43).

The process may return back to the standby state (Step ST00) upon receipt of manipulation for cancelling the falling asleep mode M01 (Step ST41) in the falling asleep detection operation (Step ST10). The process may return back to the standby state (Step ST00) upon receipt of manipulation for cancelling the falling asleep mode M01 (Step ST42) in Step ST20.

The control unit may continue the falling asleep detection operation HS0 (Step ST10) upon detection of at least one of states where the user 81 wakes up and the user is away from the bed (Step ST31) in the falling asleep detection operation (Step ST10). The process may return back to the falling asleep detection operation HS0 (Step ST10) upon detection of at least one of states where the user 81 wakes up and the user is away from the bed (Step ST33) in Step ST27. The process may return back to the standby state (Step ST00) upon detection of a state where the user 81 is away from the bed and upon lapse of a predetermined period in the falling asleep detection operation (Step ST10).

As has been described, the control unit may iterate the first falling asleep operation HS1 and the second falling asleep operation HS2. For example, as illustrated in FIG. 15, when the first round's predetermined period D1 elapses, the control unit performs the judgment operation Dc2 in the first round's first falling asleep operation HS1 as described above. For example, the control unit performs the second falling asleep operation HS2 according to the judgment operation Dc2, for example. Then, the control unit performs the second round's first falling asleep operation HS1. When the second round's predetermined period (period D2) elapses, the control unit performs the judgment operation Dc2 in the second round's first falling asleep operation HS1. In this judgment operation Dc2, the following first difference is evaluated. The first difference indicates the difference between the signal SS in a second period p21 and the signal SS in a second prior period p20 prior to the second period p21, for example. Alternatively, the first difference may be the difference between the signal SS in the second period p21 and the signal SS in a period prior to the second period p21 (e.g. the first period p11), for example. The control unit performs the second round's judgment operation Dc2 based on the result of the first difference.

The control unit performs the second round's second falling asleep operation HS2 based on the result of the second round's judgment operation Dc2, then further performs the judgment operation when the third round's predetermined period (period D3) elapses, and then performs the third round's first falling asleep operation HS1.

In the third round's judgment operation, the following second difference is evaluated. The second difference indicates the difference between the signal SS in a third period p31 and the signal SS in a third prior period p30 prior to the third period p31 in the third round's first falling asleep operation HS1, for example. Alternatively, the second difference may be the difference between the signal SS in the third period p31 in the third round's first falling asleep operation HS1 and the signal SS in a period prior to the third period p31 (e.g. the second period p21). The second difference is evaluated, and the control unit performs the third round's judgment operation based on the result of the second difference.

In this way, the control unit detects the user 81's sleep state, and performs the second falling asleep operation HS2 (user's back control) to a slight degree when the user 81's sleep is deep. This makes it possible to inhibit the user 81 from being woken up by the second falling asleep operation HS2. By iterating the above cycle, the section 71 turns flat, for example. The mattress 76 turns flat, for example. In the flat state, the user 81 can roll over easily. Then, the control unit may perform operations such as the first operation OP1 and the second operation OP2 described in relation to FIG. 4A and FIG. 4B, for example. The control unit may further perform the third operation OP3.

The above Steps ST20 to ST27 may be performed in the second operation OP2 (the decrease of inclination).

As has been described, the second angle θ2 is equal to or larger than 3 degrees and equal to or smaller than 10 degrees, for example. The inclination of the section 71 (the section angle θ) may be set at the second angle θ2 when the control unit transitions to the first falling asleep operation HS1 (Step ST20). The user 81 can fall asleep easily when the section 71 (the back section 70a) inclines gently (the second angle θ2, for example).

In another example according to the embodiments, as illustrated in FIG. 15, the control unit may evaluate, in the falling asleep detection operation HS0, the variations ΔS of the signal SS, corresponding to the biological signal of the user 81, in two successive periods (e.g. a period p_M and a prior period p_(M−1)) between the first time t01 and the second time t02. The control unit may perform the judgment operation Dc1 or the second falling asleep operation HS2 based on this evaluation result. In this case, the sleep of the user 81 of the motorized furniture is also detected at the first time t01. The control unit transitions to the first falling asleep operation HS1 at the second time t02 after the first time t01. The user 81's sleep state at the second time t02 satisfies at least one of first and second conditions. The first condition is that the elapse of time from the first time t01 to the second time t02 is equal to or larger than the first time threshold. The second condition is satisfied when the absolute value of the difference between the variations ΔS of the signal SS, corresponding to the biological signal of the user 81, in the two successive periods (e.g. the period p_M and the prior period p_(M−1)) between the first time t01 and the second time t02 is smaller than a threshold (second condition threshold).

In this way, in another example of the embodiments, the control unit may transition from the falling asleep detection operation HS0 to the first falling asleep operation HS1 based on not only the elapse of time since the first time t01 but also the degree of stability of the signal SS during the falling asleep detection operation HS0.

In this example, the control unit 42 also performs the second falling asleep operation HS2 when the variation ΔS of the signal SS in the first period p11 during the first falling asleep operation HS1 satisfies the predetermined condition (signal variation condition). As illustrated in FIG. 15, this condition is satisfied when the variation ΔS of the signal SS in the first period p11 is smaller than the variation ΔS in the period prior to the first period (e.g. the first prior period p10) or when the absolute value of the difference between the variation ΔS in the first period p11 and the variation ΔS in the above prior period (e.g. the period p_M) is smaller than the first variation threshold.

In this case, in the second falling asleep operation HS2, the control unit 42 also performs at least one of: the operation of decreasing the inclination of the section 71 of the motorized furniture; the operation of decreasing the gap between the height of the head part 77a of the mattress 76 of the motorized furniture and the height of the waist part 77b of the mattress; and the operation of decreasing the difference between the pressure in the head part 77a and the pressure in the waist part 77b.

In this case, the control unit also detects the user 81's sleep state, and performs the second falling asleep operation HS2 (user's back control) to a slight degree when the user 81's sleep is deep. This makes it possible to inhibit the user 81 from being woken up by the second falling asleep operation HS2.

In this example, the above prior period may be a period during the first falling asleep operation HS1. The above prior period may be a period between the first time t01 and the second time t02 (e.g. a period during the falling asleep detection operation).

Figure 16:
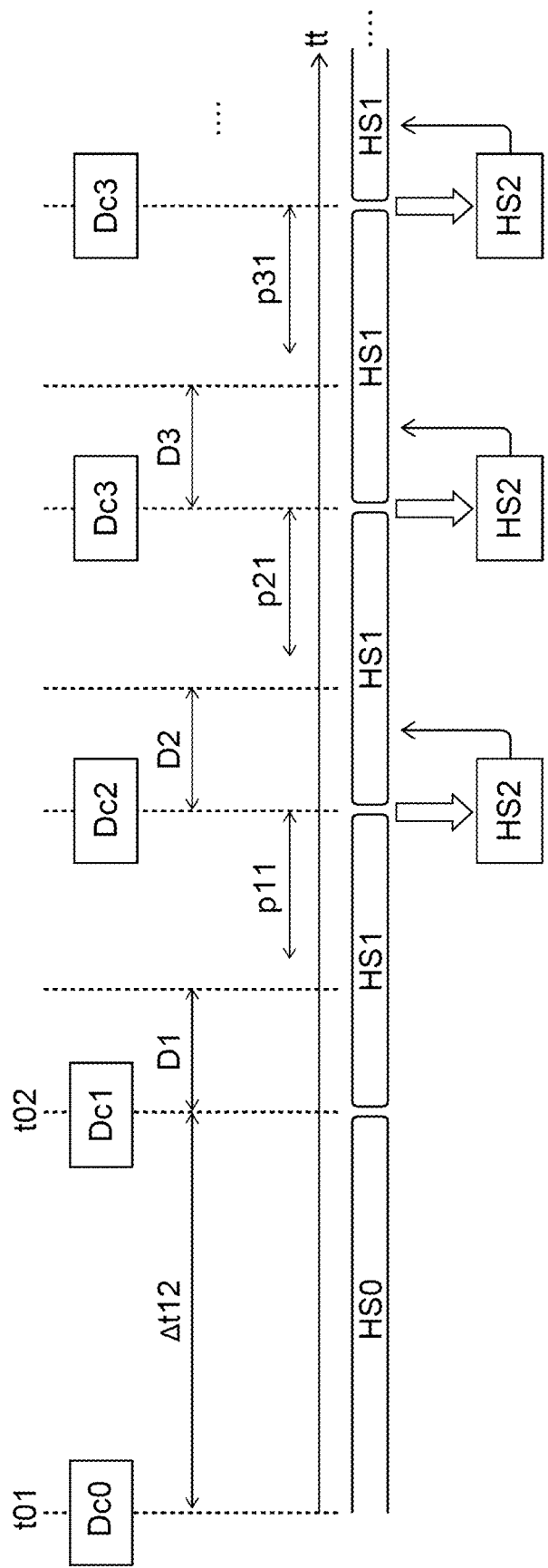
FIG. 16 is still another schematic diagram illustrating the operations of the motorized furniture according to the embodiments.

FIG. 16 is still another schematic diagram illustrating the operations of the motorized furniture according to the embodiments.

In the example illustrated in FIG. 16, as is the case with the above, the control unit 42 performs the judgment operation Dc1 at the second time t02. The control unit transitions from the falling asleep detection operation HS0 to the first failing asleep operation HS1 at the second time t02.

As illustrated in FIG. 16, the predetermined time D1 elapses after the second time t02. After the predetermined time D1 elapses, the control unit 42 performs the judgment operation Dc2. In this example, the signal SS in the first period p11 is detected. If the signal SS detected in the first period p11 satisfies the predetermined condition, the control unit 42 performs the second falling asleep operation HS2 described above (Step ST26 in FIG. 14). In this example, in Step ST21 of FIG. 14, the variation ΔS of the signal SS in the first period p11 during the first falling asleep operation HS1 is used as the variation of the biological signal, for example, and this variation ΔS is compared with the predetermined value (the first variation threshold).

For example, when the signal SS is the heartbeat rate, it is detected that the heartbeat rate in the predetermined range is calculated successively three times in the first period p11. Based on this result, the control unit 42 performs the second falling asleep operation HS2. As has been described, in the second falling asleep operation HS2, the control unit 42 performs at least one of: the operation of decreasing the inclination of the section 71 of the motorized furniture 310; the operation of decreasing the gap between the height of the head part 77a of the mattress 76 of the motorized furniture 320 and the height of the waist part 77b of the mattress; and the operation of decreasing the difference between the pressure in the head part 77a and the pressure in the waist part 77b.

As illustrated in FIG. 16, after the predetermined time D2 elapses after the judgment operation Dc2, the control unit 42 performs the judgment operation Dc3. In this example, the signal SS in the second period p21 prior to the judgment operation Dc3 is detected. For example, if the difference between the signal SS in the second period p21 and the signal SS in the first period p11 satisfies the predetermined condition, the control unit 42 performs the second round's second falling asleep operation HS2.

As illustrated in FIG. 16, after the predetermined time D3 elapses after the judgment operation Dc3, the control unit 42 performs the second round's judgment operation Dc3. In this example, the signal SS in the third period p31 prior to the second round's judgment operation Dc3 is detected. For example, if the difference between the signal SS in the third period p31 and the signal SS in the second period p21 satisfies the predetermined condition, the control unit 42 performs the third round's second falling asleep operation HS2.

In this way, the judgment operation Dc3 may be iterated multiple times after the judgment operation Dc2. By iterating the judgment operation Dc3 multiple times, the inclination of the section 71 is slowly decreased little by little, for example.

Iterating the above judgment operation multiple times corresponds to iterating the processing from Step ST20 to Step ST27 in FIG. 14 multiple times, for example. In the iteration of the processing multiple times, the "variation of the biological signal" and the "first variation threshold" in Step ST21 may be changed, for example. In the example of FIG. 16, in the initial judgment, the variation ΔS of the signal SS in the first period p11 is compared with the predetermined value. Then, in the second or later judgment, the variation ΔS between the corresponding period and the period prior to this period is compared with the predetermined value.

The embodiments can provide a motorized furniture capable of facilitating ease of use when the user falls asleep.

The reference signs in the drawings are as follows.

15: cable, 20: manipulation reception unit, 42: control unit, 43: acquisition unit, 48: storage unit, 60: detection unit, 62: sensor, 62*a*: circuit unit, 62*b*: sensor unit, 62*c*: communication unit, 62*d*: sensor device, 62*p*: first platy body, 62*q*: second platy body, 62*r*: air housing body, 62*s*: support protrusion, 62*t*: groove, 62*u*: signal line, 62*v*: detection circuit, 70: movable unit, 70B: bed part, 70C: controlled unit, 70*a*: back section, 70*b*: upper leg section, 70*c*: lower leg section, 70*d*: head section, 70*g*: caster, 70*h*: height change section, 70*p*: backrest part, 70*q*: seating face part, 71: section, 72: driving unit, 73*a*: lighting unit, 73*b*: temperature control unit, 74: bed leg part, 75: frame, 76: mattress, 76*a*: air cell, 76*b*: pump unit, 76*c*: cable, 76*d*: mattress manipulation unit, 76*e*: cable, 76*f*: mattress driving unit, 77*a*: head part, 77*b*: waist part, 77*c*: foot part, 81: user, ΔS, ΔS1, ΔS2: variation, Δt12: elapse of time, θ: section angle, θ1 and θ2: first to third angles, 160: control device, 310, 320, 330, 340: motorized furniture, D1, D2, D3: time, Dc0, Dc1, Dc2, Dc3: judgment operation, H1, HR: height, HS0: falling asleep detection operation, HS1, HS2: first and second falling asleep operations, M01: falling asleep mode, OP1 to OP3: first to third operations, Ops: falling asleep operation, SC: control signal, SM: signal, SS: signal, Tm: temperature, mt1, mt2: first and second mattress states; p_(M−1): prior period, p_M: period, p10, p20, p30: first to third periods, p11, p21, p31: first to third periods, st1, st2: first and second signal states, t01: first time, t02: second time, t1: time, tm: time, ts: time, tt: time.

The embodiments may include the following configuration (e.g. technique) ideas, for example.

(Configuration 1)

A motorized furniture including a control unit, in which
the control unit transitions to a first falling asleep operation at second time where the elapse of time since first time, where the sleep of a user of the motorized furniture is detected, is equal to or larger than a first time threshold,
the control unit performs a second falling asleep operation when a variation of a signal corresponding to a biological signal of the user in a first period during the first falling asleep operation is smaller than the variation in a first prior period, which exists prior to the first period, during the first falling asleep operation or when the absolute value of a difference between the variation in the first period and the variation in the first prior period is smaller than a first variation threshold, and
in the second falling asleep operation, the control unit performs at least one of: an operation of decreasing the inclination of a section of the motorized furniture; an operation of decreasing the gap between the height of a head part of a mattress of the motorized furniture and the height of a waist part of the mattress; and an operation of decreasing the difference between the pressure in the head part and the pressure in the waist part.

(Configuration 2)

A motorized furniture including a control unit, in which
the control unit transitions to a first falling asleep operation at second time after first time where the sleep of a user of the motorized furniture is detected, the state of the sleep of the user at the second time satisfies at least one of a first condition and a second condition, the first condition is that the elapse of time from the first time to the second time is equal to or larger than a first time threshold, the second condition is satisfied when the absolute value of a difference between variations of a signal, corresponding to a biological signal of the user, in two successive periods between the first time and the second time is smaller than a threshold of the second condition,
the control unit performs a second falling asleep operation when the variation in a first period during the first falling asleep operation is smaller than the variation in a period prior to the first period or when the absolute value of a difference between the variation in the first period and the variation in the prior period is smaller than a first variation threshold, and
in the second falling asleep operation, the control unit performs at least one of: an operation of decreasing the inclination of a section of the motorized furniture; an operation of decreasing the gap between the height of a head part of a mattress of the motorized furniture and the height of a waist part of the mattress; and an operation of decreasing the difference between the pressure in the head part and the pressure in the waist part.

(Configuration 3)

The motorized furniture described in the configuration 2, in which the prior period exists during the first falling asleep operation.

(Configuration 4)

The motorized furniture described in the configuration 2, in which the prior period exists between the first time and the second time.

(Configuration 5)

The motorized furniture described in any one of the configurations 1 to 4, in which the control unit iterates the first falling asleep operation and the second falling asleep operation.

(Configuration 6)

The motorized furniture described in any one of the configurations 1 to 5, in which
in the second falling asleep operation, the control unit performs the operation of decreasing the inclination of the section of the motorized furniture, and
the difference between the angle of the section after the decrease of inclination and the angle of the section in a period prior to the decrease of inclination is 1 degree or smaller.

(Configuration 7)

The motorized furniture described in any one of the configurations 1 to 6, in which
the motorized furniture further includes a manipulation reception unit that is capable of communicating with the control unit, and
once the manipulation reception unit receives manipulation, the control unit starts detecting the sleep of the user.

(Configuration 8)
The motorized furniture described in any one of the configurations 1 to 6, in which the control unit starts detecting the sleep of the user at preset time.

(Configuration 9)
The motorized furniture described in any one of the configurations 1 to 8, in which the control unit finishes the first falling asleep operation if at least one of states where the user wakes up and the user is away from the bed continues for a second time threshold or longer.

(Configuration 10)
The motorized furniture described in any one of the configurations 1 to 8, in which the control unit finishes the second falling asleep operation if at least one of states where the user wakes up and the user is away from the bed continues for a second time threshold or longer.

(Configuration 11)
The motorized furniture described in any one of the configurations 1 to 8, in which the control unit finishes detecting the sleep of the user if at least one of states where the user wakes up and the user is away from the bed continues for a second time threshold or longer.

(Configuration 12)
The motorized furniture described in any one of the configurations 1 to 11, in which the length of the first period is equal to or longer than 10 seconds and equal to or shorter than 5 minutes.

(Configuration 13)
The motorized furniture described in any one of the configurations 1 to 12, in which the first time threshold is equal to or longer than 5 minutes and equal to or shorter than 30 minutes.

(Configuration 14)
The motorized furniture described in any one of the configurations 1 to 13, in which the signal includes information on the heartbeat rate of the user.

(Configuration 15)
The motorized furniture described in any one of the configurations 1 to 13, in which the signal includes information on the respiratory rate of the user.

(Configuration 16)
The motorized furniture described in any one of the configurations 1 to 13, in which the signal includes information on at least one of motions of the arms, torso, and feet of the user.

(Configuration 17)
The motorized furniture described in any one of the configurations 1 to 13, in which the signal includes information on the rolling over of the user.

(Configuration 18)
The motorized furniture described in the configuration 1, in which, in the first falling asleep operation, the control unit does not perform the second falling asleep operation if the absolute value is equal to or larger than the first variation threshold.

(Configuration 19)
The motorized furniture described in the configuration 1, in which the control unit does not perform the second falling asleep operation if the variation in the first period during the first falling asleep operation is smaller than the variation in the first prior period.

(Configuration 20)
The motorized furniture described in any one of the configurations 1 to 19, in which
after the first falling asleep operation and the second falling asleep operation, the signal includes a first signal state and a second signal state,
the variation of the signal in the second signal state is smaller than the variation of the signal in the first signal state, and
when the signal becomes the first signal state at the time before and closest to predetermined time, the control unit sets the inclination of the section larger than the inclination increased.

According to the embodiments, it is possible to provide a motorized furniture capable of facilitating ease of use.

The embodiments of the present invention have been described above with reference to the specific examples. However, the present invention is not limited to these specific examples. For example, any specific configuration of the constituents, such as the control unit, the acquisition unit, the movable unit, the section, and the mattress, included in the motorized furniture falls within the scope of the present invention as long as such a configuration is selected appropriately by those skilled in the art within a known range and can implement the present invention in the same way as those in the specific examples and bring about the same effect as those in the specific examples.

Any combination of any two or more constituents of the specific examples that are combined within a technically possible range also falls within the scope of the present invention as long as such a combination includes the essence of the present invention.

In addition, any motorized furniture that those skilled in the art can embody by appropriately changing the design of the motorized furniture described above in the embodiments of the present invention also falls within the scope of the present invention as long as such a motorized furniture includes the essence of the present invention.

Besides, those skilled in the art can conceive of various change examples and modification examples within the concept of the present invention, and such change examples and modification examples are also deemed to fall within the scope of the present invention.

The invention claimed is:

1. A furniture comprising:
a moveable part;
a sensor configured to detect a signal corresponding to a body movement of a user; and
a controller configured to
determine whether a change of the signal increases or decreases after the user is falling asleep, a state of the signal being a first state or a second state,
automatically perform a first operation in response to determining that the change of the signal increases and the signal being in the first state closest to a given time, the first operation including raising a of the moveable part, and
automatically perform a second operation in response to determining that the change of the signal increases and the signal not being in the first state closest to the given time, the second operation including lowering a tilt of the moveable part.

2. The furniture according to claim 1, wherein the controller is configured to change the tilt of the moveable part based on a history of the change of the signal associated with a history of the tilt of the moveable part.

3. The furniture according to claim 2, wherein the controller includes a standby mode and a sleeping mode, and the controller is configured to control the sensor to acquire the signal in the sleeping mode.

4. The furniture according to claim 1, wherein the controller includes a standby mode and a sleeping mode, and the controller is configured to control the sensor to acquire the signal in the sleeping mode.

5. The furniture according to claim 4, wherein the controller is configured to automatically perform the second operation in response to the change of the signal decreasing in the sleeping mode.

6. The furniture according to claim 1, wherein the controller is configured to:
control the sensor to acquire the signal in response to the controller not receiving an instruction from the user; and
not perform the second operation in response to receiving an instruction from the user.

7. The furniture according to claim 6, wherein the controller is configured to:
automatically perform the second operation in response to the controller not receiving an instruction from the user; and
not perform the second operation in response to receiving an instruction from the user.

8. The furniture according to claim 7, wherein the controller is configured to control the moveable part so as to execute the instruction from the user.

9. The furniture according to claim 8, wherein the controller is configured to:
perform the second operation in response to the change of the signal decreasing; and
suspend the second operation and control the moveable part so as to execute the instruction from the user in response to receiving the instruction from the user during the second operation.

10. The furniture according to claim 7, wherein the controller is configured to:
perform the second operation in response to the change of the signal decreasing; and
suspend the second operation and control the moveable part so as to execute the instruction from the user in response to receiving the instruction from the user during the second operation.

* * * * *